United States Patent [19]
Suzuki et al.

[11] Patent Number: 5,316,727
[45] Date of Patent: May 31, 1994

[54] MEASURING APPARATUS

[75] Inventors: Yoshiro Suzuki, Yamanashi; Hitoshi Tanaka, Yokohama; Noriyuki Kurihara, Chigasaki; Yutaka Saito, Yokosuka, all of Japan

[73] Assignees: Terumo Kabushiki Kaisha; Yamatake-Honeywell Co., Ltd., both of Tokyo, Japan

[21] Appl. No.: 936,079

[22] Filed: Aug. 28, 1992

Related U.S. Application Data

[63] Continuation of Ser. No. 578,641, Sep. 7, 1990, abandoned.

[30] Foreign Application Priority Data

| Sep. 8, 1989 | [JP] | Japan | 1-231538 |
| Sep. 8, 1989 | [JP] | Japan | 1-231539 |
| Sep. 8, 1989 | [JP] | Japan | 1-231541 |
| Sep. 8, 1989 | [JP] | Japan | 1-231543 |

[51] Int. Cl.$^5$ ............................................. G01N 21/01
[52] U.S. Cl. ..................... 422/68.1; 356/39; 356/40; 356/41; 356/42; 422/82.01; 422/82.05; 422/82.09
[58] Field of Search ................ 422/68.1, 82.05, 82.01, 422/82.09; 356/39, 40, 41, 42

[56] References Cited

U.S. PATENT DOCUMENTS

| 4,558,013 | 12/1985 | Marinkovich et al. | 422/82.09 |
| 4,637,403 | 1/1987 | Garcia et al. | 128/770 |
| 4,731,726 | 3/1988 | Allen, III | 364/416 |
| 4,873,993 | 10/1989 | Meserol et al. | 356/39 |
| 4,934,817 | 6/1990 | Gassenhuber | 422/68.1 |
| 5,037,614 | 8/1991 | Makita et al. | 422/68.1 |

FOREIGN PATENT DOCUMENTS

| 20876/83 | 11/1983 | Australia . |
| 0272407 | 6/1988 | European Pat. Off. . |
| 0283285 | 9/1988 | European Pat. Off. . |
| 3432972 | 3/1986 | Fed. Rep. of Germany . |
| 3701192 | 4/1988 | Fed. Rep. of Germany . |
| WO83/00926 | 3/1983 | PCT Int'l Appl. . |
| WO86/05966 | 10/1986 | PCT Int'l Appl. . |
| WO88/00812 | 2/1988 | PCT Int'l Appl. . |

OTHER PUBLICATIONS

Patent Abstracts of Japan, vol. 11, No. 164, (P-580) [2611] May 27, 1987 Omron Tateisi Electronics Co.
Patents Abstracts of Japan, vol. 11, No. 109, (P-564) [2556], Apr. 7, 1987 Konishiroku Photo Ind. Co. Ltd.
Patent Abstracts of Japan, vol. 10, No. 232, (P-486) [2288], Aug. 12, 1986 Omron Tateisi Electronics Co.

Primary Examiner—Timothy M. McMahon
Attorney, Agent, or Firm—Burns, Doane, Swecker & Mathis

[57] ABSTRACT

A measuring apparatus of the present invention measures the constituent concentration of a specimen after loading into the apparatus a test piece having a test material which develops coloring as a result of a reaction with the constituents of a specimen. When the apparatus detects that the test piece having the test material has been loaded, it automatically begins to measure the constituent concentration of the specimen. That is, after the loading of the test piece is detected, a predetermined time period is measured. During this time measurement, the time period is displayed at a predetermined time interval. After the time measurement of this predetermined time period is terminated, the test material is irradiated with a light, and the intensity of the light from the test material is detected. The constituent concentration of the specimen applied to the test material can be determined on the basis of the reflected light intensity thus detected. Furthermore, this measuring apparatus can detect a reverse insertion of a test piece, and is constructed so as to disable the measurement of the constituent concentration of a specimen if supplementary information to be stored along with measurement information has not been set.

9 Claims, 18 Drawing Sheets

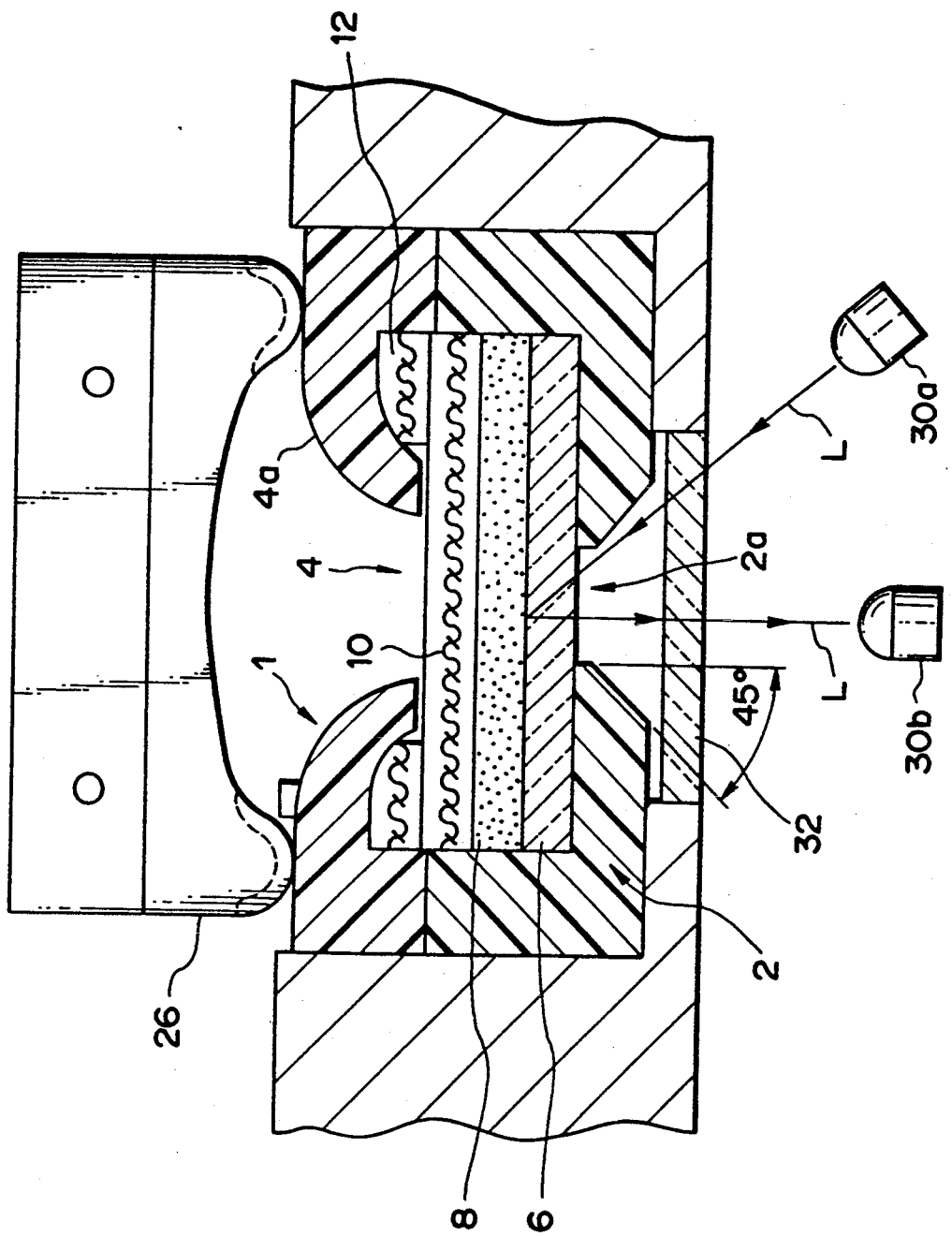

MEASURING APPARATUS

This application is a continuation of application Ser. No. 07/578,641, filed Sep. 7, 1990 now abandoned.

BACKGROUND OF THE INVENTION

1. Field of the Invention

The present invention relates to a measuring apparatus which measures the constituent concentration of a specimen after the specimen to be measured is applied to a test material of a test piece and the test piece is loaded, for example, a measuring apparatus which determines the concentration of constituents in blood.

2. Description of the Related Art

In a conventional blood constituent measuring apparatus, first blood to be measured is applied to test paper, and the test paper is loaded into the measuring apparatus. Then after lapse of a predetermined time period necessary for the test paper to react to the constituents of the blood, a measurement is started. Such test paper is generally housed in a small disposable container called a test piece in view of its maneuverability. A specimen of a substance to be measured, for instance, blood, is applied to test paper through an opening formed through this container, and the test piece together with this container are loaded into the apparatus. In this way, after loading this container into the apparatus, the test paper is irradiated with a light through an opening formed on the rear side of the opening, and the constituent concentration of a specimen is determined by measuring the reflected light intensity.

However, in the example of the prior art, even if the container is reversely loaded into the apparatus erroneously, the result of a measurement is output after the lapse of a predetermined time when the reaction of the test paper is completed, with the result that the fact that the container has been reversely loaded can be determined by an abnormal measurement result. For this reason, at the time this reverse insertion is found, since more than the predetermined time period has elapsed after the test paper had reacted to the blood, the test paper cannot be used again for a measurement, and therefore a measurement must be repeated from the beginning using another test paper. Further, the abnormal measurement result caused by a reverse insertion will be announced to the person under measurement as his result.

Of such conventional measuring apparatuses which measure constituents of a specimen, particularly in a blood sugar measuring apparatus, a test piece is loaded to a measuring apparatus after blood to be measured is applied to test paper of a test piece and excessive blood is wiped off, and after the lapse of a predetermined time when the test paper reacts to the blood constituents. After the loading is complete, by depressing a measurement start switch disposed on the measuring apparatus, a measurement of a blood sugar value is started.

In the above-mentioned example of the prior art, however, the predetermined time period until the test paper reacts must be measured by an operator, who is troubled by such operation. Thus, a mistake in measuring time may result in an inaccurate blood sugar value. Also, if the start switch is not depressed, a measurement is not started after the loading of a test piece. Therefore, even if time is measured accurately with much effort, a measurement cannot be made because the depressing of the start switch is forgotten. Or, a delay in depressing the start switch also result in an inaccurate blood sugar value.

Blood sugar values which have been measured in the above way are stored in a memory or the like of the apparatus together with measurement date and time information. The measurement date and time information stored along with such measurement result is very important information in taking a history of the blood sugar values of a person. In the conventional measuring apparatus, however, since a measurement can be made even if the date and time information is not set, and the information is stored in the memory, the stored blood sugar value itself is meaningless since the date when the information was measured is unknown.

SUMMARY OF THE INVENTION

The present invention has been devised in light of the above-mentioned examples of the prior art. An object of the present invention is to provide a measuring apparatus which is capable of immediately detecting and announcing whether or not a test piece is normally loaded when the test piece, to which a specimen to be measured is applied, is loaded into the measuring apparatus.

In order to achieve the above-mentioned objects, the measuring apparatus of the present invention which measures the constituent concentration of the specimen after the loading the test piece having a test material which develops coloring as a result of a reaction with the constituents of the specimen, comprises detection means for detecting reflected light from the test material by irradiating the test material with light; determination means for determining the constituent concentration of the specimen on the basis of the reflected light intensity detected by the detection means; test piece detection means for detecting whether the test piece has been loaded into the apparatus's main body; judgment means for judging whether or not the intensity of the reflected light from the detection means is within a predetermined range when the loading of the test piece is detected by the test piece detection means; and notifying means for notifying that a measurement using the test piece is impossible when the reflected light intensity is judged to be out of the predetermined range by the judgment means.

Another object of the present invention is to provide a measuring apparatus which is capable of easily and accurately measuring specific constituents of a specimen only by loading a test material applied with the specimen into the measuring apparatus.

In order to achieve the above-mentioned objects, the measuring apparatus of the present invention is an apparatus which measures the constituents of a specimen on the basis of the reaction color of a test material which changes in color as a result of a reaction with the constituents of the specimen, comprises irradiation means for irradiating the test material with light; detection means for detecting light reflected from the test material of the light emitted by the irradiation means; measurement means for determining the constituent concentration of a specimen applied to the test material on the basis of a detection signal from the detection means; test piece detection means for detecting whether the test piece having the test material has been loaded into the main body of the apparatus; and control means for controlling so as to allow the measurement means to when the loading of the test piece is detected by the test piece detection means.

A further object of the present invention is to provide a measuring apparatus which is capable of easily and accurately measuring specific constituents of a specimen only by loading a test material applied with the specimen into the measuring apparatus, and which is capable of informing an operator that a measurement is being made by displaying a time period required for the measurement.

In order to achieve the above-mentioned objects, the measuring apparatus of the present invention is an apparatus which measures the constituent concentration of a specimen on the basis of the color developed by a test material after loading a test piece which includes the test material which develops color because of the constituents of a specimen, comprises detection means for detecting whether the test piece has been loaded; time measuring means for measuring a predetermined time period and displaying it at a predetermined time interval after it has been determined by the detection means that the test piece has been loaded; and measuring means for reading the degree of the coloring developed by the test material and for determining the constituent concentration of the applied specimen by photoelectrically reading out the degree of the coloring developed by the test material when the predetermined time period is measured by the time measuring means.

A still further object of the present invention is to provide a measuring apparatus which is capable of informing an operator of completion of a measurement or proximity of completion of a measurement.

A still further object of the present invention is to provide a measuring apparatus which is capable of effectively utilizing a measured constituent concentration by prohibiting the measurement when supplementary information to be stored along with the measured constituent concentration has not been set.

In order to achieve the above-mentioned objects, the measuring apparatus of the present invention is an apparatus which measures the constituent concentration of a specimen on the basis of the color developed by a test material after loading a test piece which includes the test material which develops color because of the constituents of a specimen, comprises measuring means for photoelectrically reading the degree of the coloring developed by the test material so as to measure the constituent concentration of the applied specimen when the loading of the test piece is detected; storage means for storing results of the measurement by the measuring means together with supplementary information; setting means for inputting and setting the supplementary information; and control means for controlling so as to prohibit the measuring means from measuring when supplementary information has not been input and set by the setting means.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 4 is a cross-sectional view taken along the line A—A' of FIG. 3 in a state in which the test piece is loaded;

DESCRIPTION OF THE PREFERRED EMBODIMENTS

The preferred embodiments of the present invention will be explained in detail hereinafter with reference to the accompanying drawings.

Figure 1:
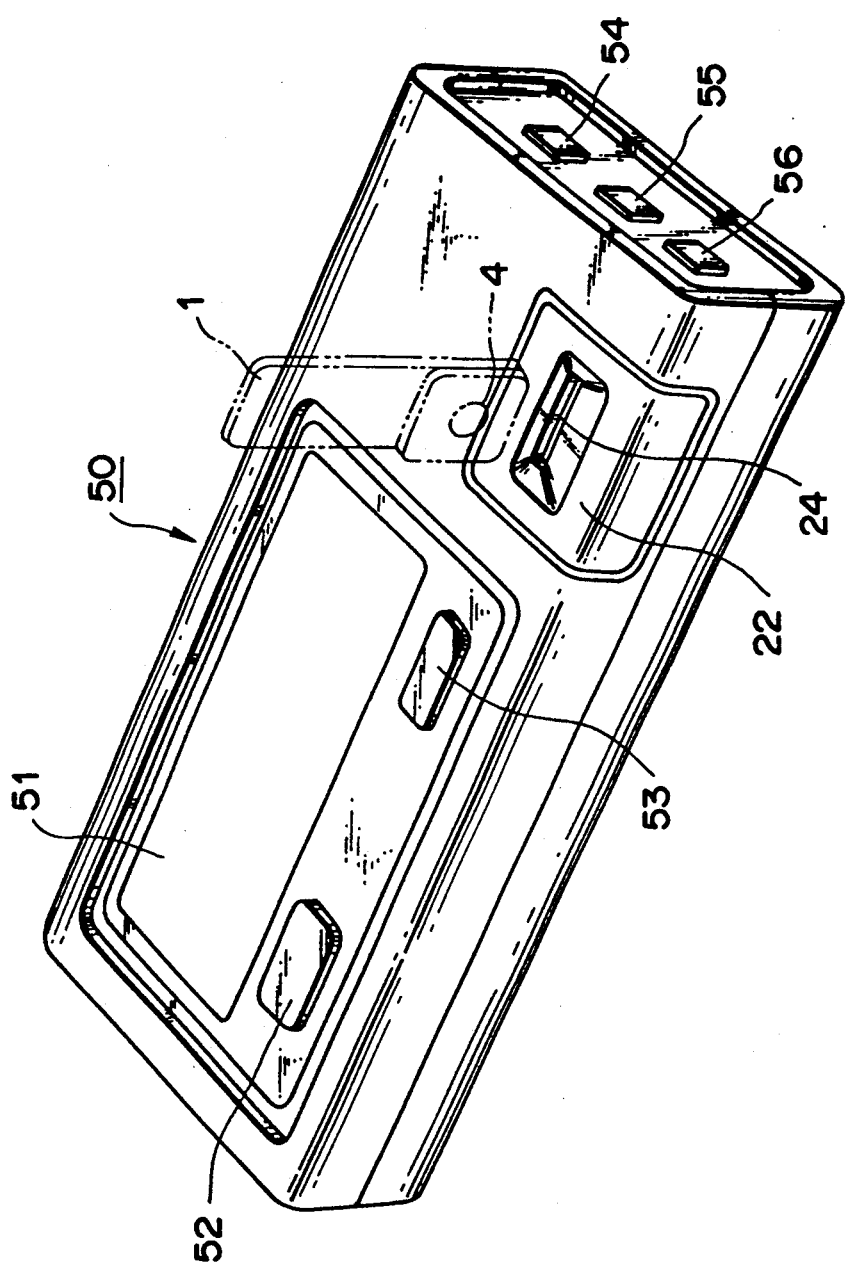
FIG. 1 is an external perspective view of the exterior of an automatic blood sugar measuring device in a first embodiment of this invention.

FIG. 1 is a external perspective view of the exterior of an automatic blood sugar measuring device 50 of the first embodiment of the present invention.

In FIG. 1, numeral 50 denotes the main body of the automatic blood sugar measuring device, 51 denotes a liquid-crystal display section for displaying measurement results, and 52 denotes a power-supply switch. The power supply of the device 50 is turned on by depressing this switch 52 when the power supply of the device 50 is off. Conversely, the power supply of the device 50 is turned off by depressing this switch 52 when the power supply of the device 50 is on. Numeral 53 denotes a storage retrieval switch. Each time the switch 53 is depressed, measurement results stored in a memory (a RAM 74 in FIG. 2) disposed in the device are read out in sequence along with measurement date and time, and are displayed on a display section 51. Numeral 1 denotes a blood sugar test piece. Blood under measurement is applied to a test paper portion in the test piece 1 through the opening 4. The test piece 1 is inserted and loaded into an opening (insertion hole) 24 of the device 50. As a result, the color of the test paper is read out photoelectrically through the opening (2a in FIG. 3) on the rear side of the opening 4 in the test piece 1, and the blood sugar value of the applied blood is measured.

Numeral 54 denotes a storage stop switch. During a measurement of a blood sugar value, when the switch 54 is not pressed within a predetermined time period after the measurement, the measured blood sugar value is automatically stored in the memory (the RAM 74). However, by pressing this switch 54 within the predetermined time period after measurement, the blood sugar value measured immediately before is not stored in the memory (the RAM 74). Thus, for example, when blood is not properly applied to the test paper, or when abnormal measurement values are obtained due to operation errors, depression of the switch 54 prevents the values from being stored in the memory (the RAM 74).

Numeral 55 denotes a setting switch. By pressing this switch 55, values of (month, day, hour, and minute) can be set and stored in the RAM 74. Numeral 56 denotes a change switch for updating a date or time as instructed by the setting switch 55.

Figure 2:
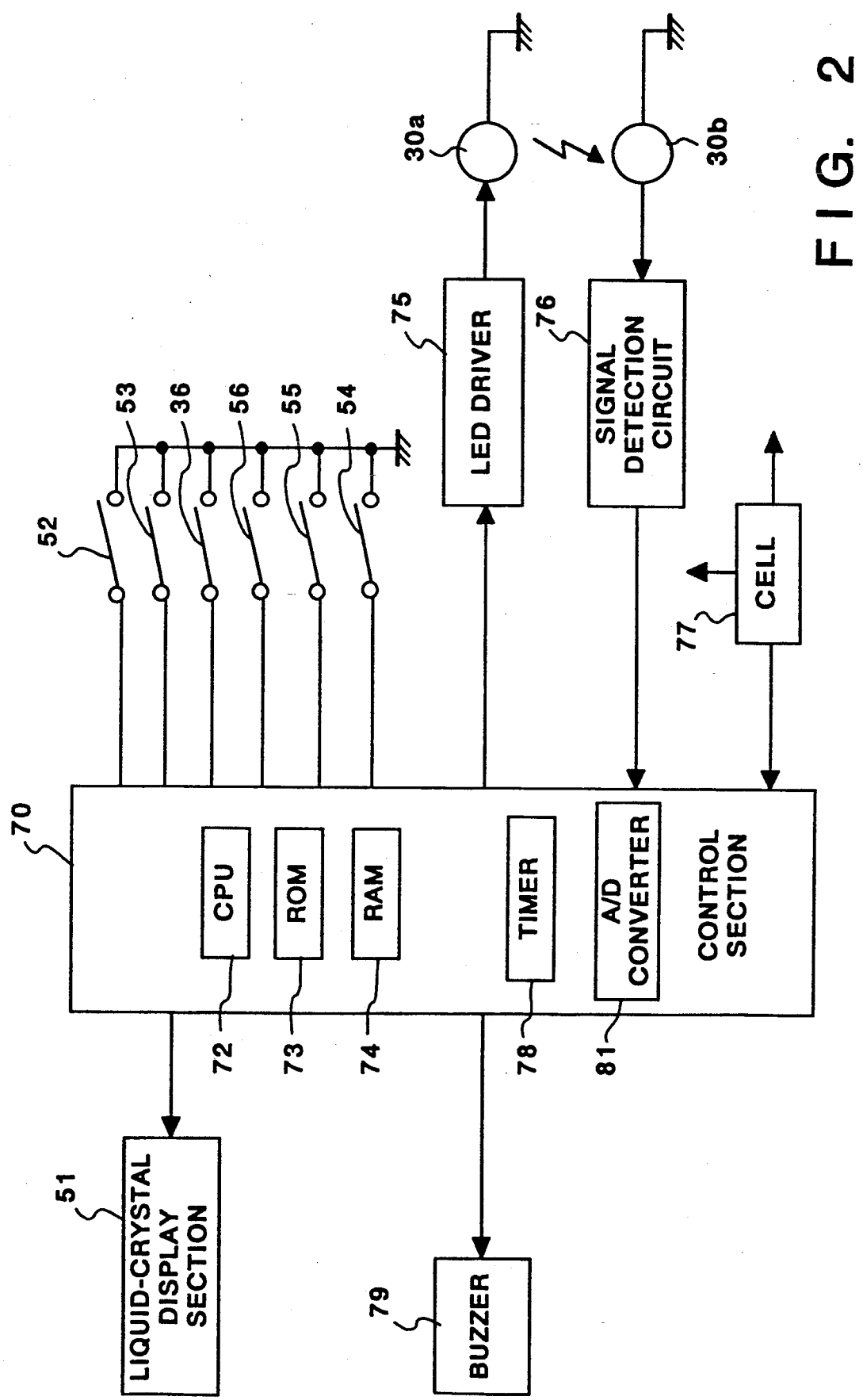
FIG. 2 is a block diagram illustrating the construction of the automatic blood sugar measuring device of the first embodiment of the present invention.

FIG. 2 is a block diagram illustrating the construction of the automatic blood sugar measuring device 50. Parts common to those of FIG. 1 are given the same numerals, and the explanation thereof is omitted.

In FIG. 2, numeral 70 denotes a control section which controls the whole device. This control section comprises a CPU 72 such as a microprocessor, a ROM 73 in which are stored control programs for the CPU 72 shown in the flowchart of FIG. 6 and various kinds of data, and a RAM 74 which is used as a work area for the CPU 72 and in which measurement results are stored along with the measurement date and time. The control section 70 accepts, as input, the status of various kinds of connected switches in order to perform an operation corresponding to these inputs. It also obtains a blood sugar value by reading a signal value from a photosensor 30b, and displays measurement results and the contents of the memory (the RAM 74) on the liquid-crystal display section 51. Numeral 36 denotes a switch for detecting whether the test piece 1 is inserted into the opening 24. The switch is turned on when the test piece 1 is inserted, thus causing a measurement of a blood sugar value to be started automatically when the power supply of the device 50 is on.

Figure 3:
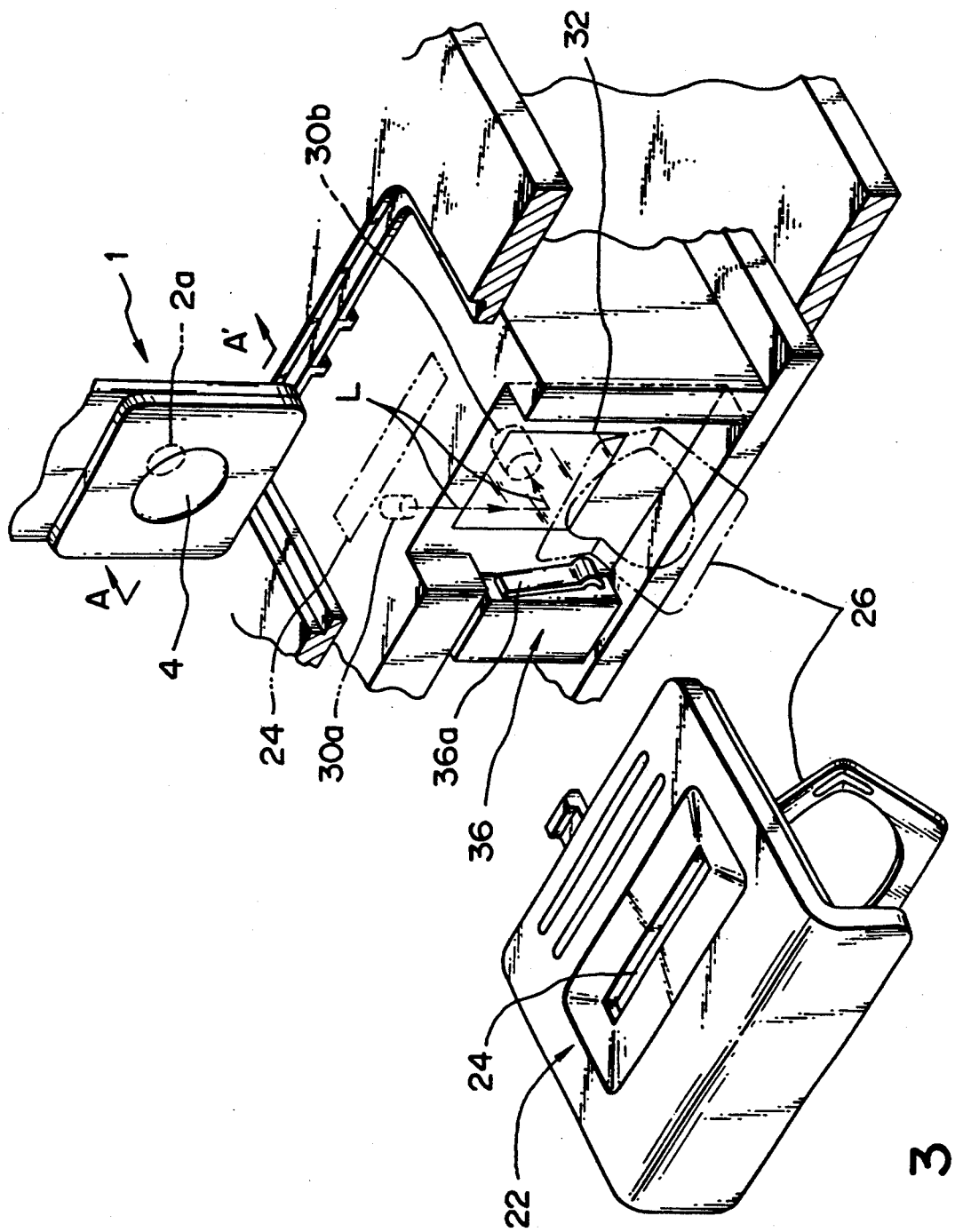
FIG. 3 is an external perspective view illustrating the details of a loading section into which a test piece is to be loaded, of the automatic blood sugar measuring device in the first embodiment of the present invention.

Numeral 75 denotes an LED driver for turning on an LED 30a with a constant current when instructions are received from the control section 70. The LED 30a irradiates the test piece 1 from the rear side (the rear side of the test piece 1 shown in FIG. 1). The reflected light is detected by means of the photosensor 30b, and the blood sugar value of the blood of the test piece 1 is determined on the basis of the intensity of the reflected light. Numeral 76 denotes a signal detection circuit for converting the intensity of the reflected light, which is detected by the photosensor 30b, into a voltage value. An analog signal from the signal detection circuit 76 is input to the control section 70 and is converted from analog to digital by means of an A/D converter 81. A digital signal corresponding to the reflected light intensity is then input to the CPU 72. Numeral 77 denotes a cell as a power supply which supplies power to the whole device 50. Numeral 78 denotes a timer disposed in the control section 70, which measures the lapse of time and measures a predetermined time by the instruction from the CPU 72. Numeral 79 denotes a buzzer which generates an alarm to operators and announces lapse of one second, a measurement termination, and errors, during the count-down display which will be described later. FIG. 3 is a external perspective view illustrating the details of the insertion section of the automatic blood sugar measuring device 50 of the embodiment, into which a test piece is to be inserted. The same parts as those shown in the above-mentioned figures are given the same numerals.

FIG. 3 shows a state in which an auxiliary cover 22 is removed from the main body 50 shown in FIG. 1. The portions indicated by the dotted lines of the opening 24 and a spring 26 for urging the test piece 1 show positions of respective sections in a state in which the auxiliary body 22 is mounted. The test piece 1 inserted in the device 50 is urged toward light-transmissive body 32 by a spring 26. Light L emitted from the LED (light-emitting diode) 30a irradiates the opening 2a of the test piece 1 through the light-transmissive body 32, and the reflected light reaches the photosensor 30b. This construction will be explained in detail with reference to FIG. 4.

Numeral 36 denotes a microswitch for detecting whether the test piece 1 is loaded. At the time the test piece 1 is loaded, an actuator 36a of the microswitch 36 is depressed by the side of the test piece 1, causing the microswitch to be turned on. As a result, the control section 30 accepts a signal from this switch 36, thereby detecting whether the test piece 1 has been completely loaded in the device 50. Since this actuator 36a does not turn on the switch 36 as long as the test piece 1 is not mounted normally, a defective loading of the test piece 1 can be detected by a signal from the switch 36.

FIG. 4 is a transverse sectional view of the measuring section illustrating a state taken along the line A—A' of FIG. 3 in which the test piece 1 is mounted on the device 50.

Blood applied through the opening 4 of the test piece 1 oozes out in a liquid developing layer 10 and infiltrates in a reagent layer (test paper) 8. Numeral 12 denotes a liquid absorbing layer for absorbing excessive blood which is not absorbed in the liquid developing layer 10. Numeral 6 denotes a light-transmissive layer for transmitting light. Light L emitted from the LED 30a passes through the light-transmissive body 32 and the light transmissive layer 6, and indicates the test paper 8. Then, reflected light from the reagent layer (test paper) 8 reaches the photosensor 30b disposed at a position forming an angle of approximately 45° with respect to the incident light. As a result, the reaction color of the test paper 8 is read out, and the blood sugar value of the blood is determined on the basis of this reaction color.

It takes approximately one minute from the time when blood is applied through the opening 4 to the time when the blood has infiltrated in the reagent layer 8 through the liquid developing layer 10 and has reacted. Hence, in this automatic blood sugar measuring device, a measurement is made one minute after the test piece 1 is inserted and loaded in the opening 24. In FIG. 4, numeral 2 denotes the main body of the test piece 1. Numeral 4a denotes a taper section formed in the opening 4 for facilitating the application of blood. Numeral 2b denotes a taper section in an opening 2a, which is formed at an angle of approximately 45°, allowing light from the LED 30a to enter.

Figures 5A, 5B:
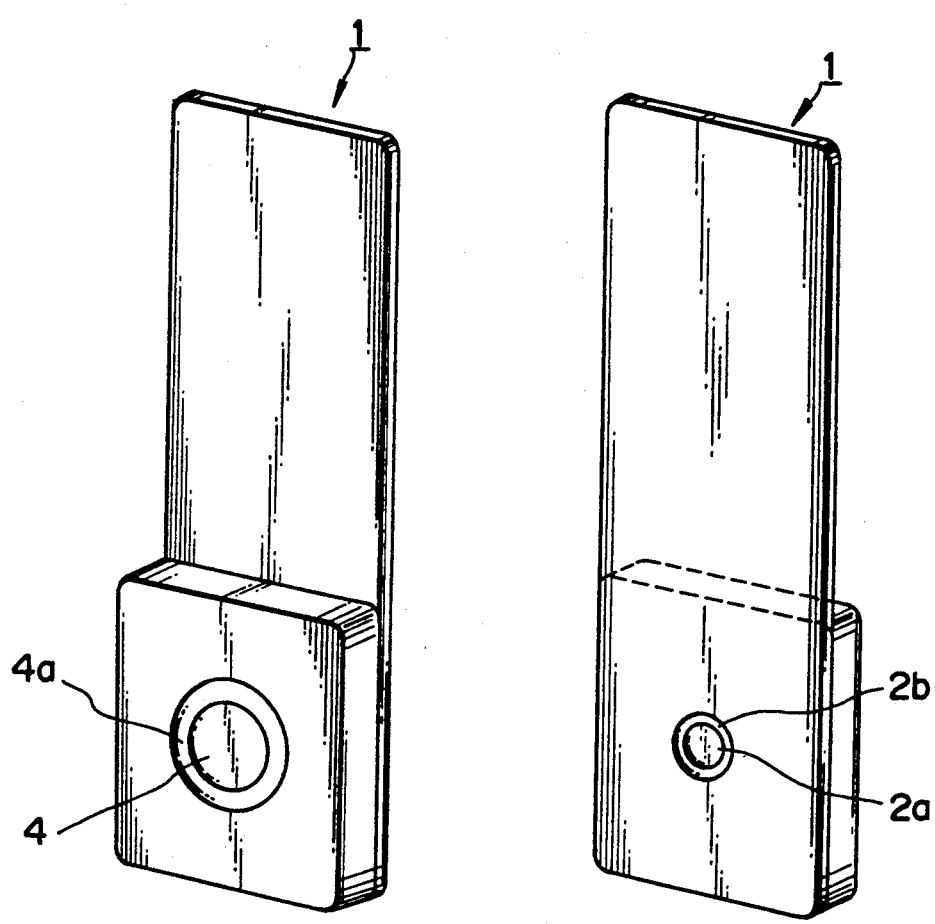
FIG. 5 is a view illustrating the exterior of the test piece in the first embodiment.

FIG. 5 is a view illustrating the exterior of the test piece 1 in the embodiment. FIG. 5(A) is a perspective view of the front side; FIG. 5(B) is a perspective view of the rear side.

Blood is applied to the opening 4, and its color is red, while the opening 2a is a color-changeable test paper side. The color of the test paper becomes darker as the reaction with blood advances with lapse of time.

Figure 6A:
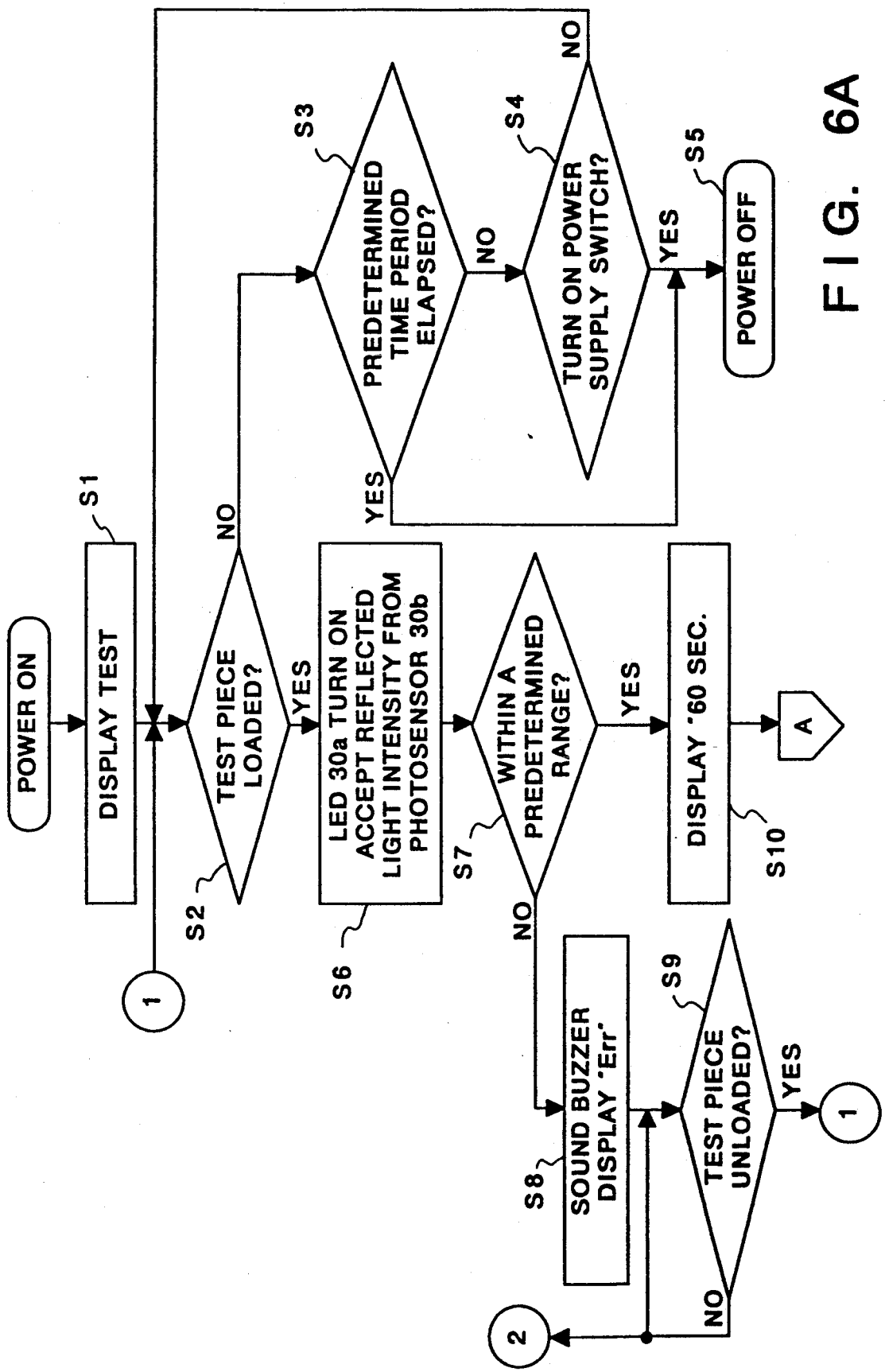
FIGS. 6A and 6B are flowcharts illustrating the measurement process in the blood sugar measuring device of the first embodiment.
Figure 6B:
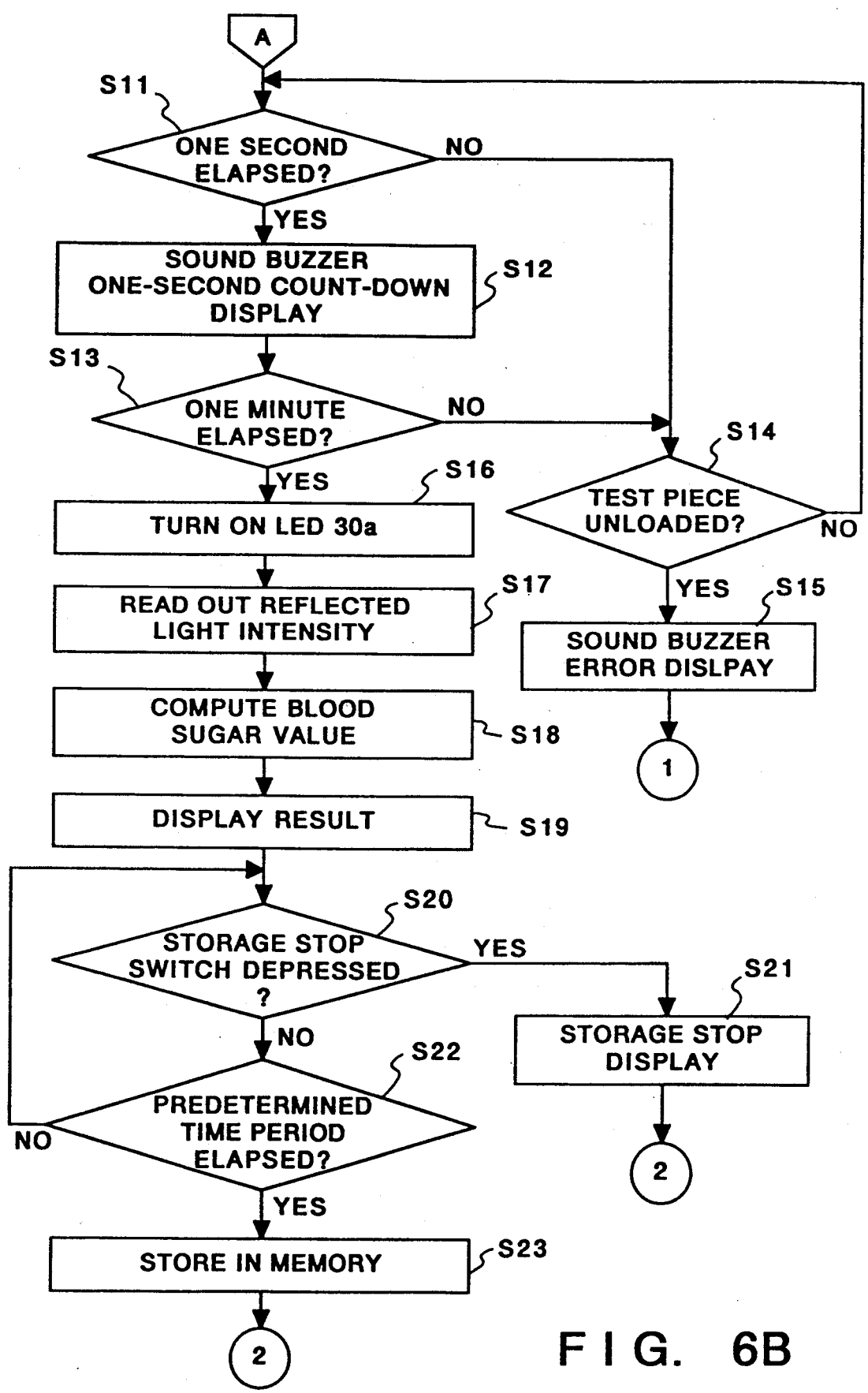

FIG. 6 is a flowchart illustrating the operations in the blood sugar measuring device of the embodiment. Control programs for executing these operations are stored in the ROM 73.

The operations shown in FIG. 6 are started when the power supply switch 52 of the device 50 is depressed to turn the power on. In step S1, all items which can be displayed are displayed on the display section 51 for several seconds to confirm whether or not the display section 51 is functioning normally. Next, the process proceeds to step S2 where whether or not the test piece 1 has been loaded is checked by determining whether or not the switch 36 is on. If the switch 36 is not on (the test piece 1 has not been loaded), the process proceeds to step S3 where it is checked whether or not a predetermined time period (e.g., five minutes) has elapsed. If the predetermined time period has elapsed, the process proceeds to step S5 where the power supply to the device is turned off If the predetermined time period has not yet elapsed in step S3, the process proceeds to step S4 where it is checked whether or not the power supply switch 52 has been depressed. When yes, the process proceeds to step S5 where the power supply is turned off.

When it is detected in step S2 that the test piece 1 has been loaded, the process proceeds to step S6 where the LED 30a is turned on, and the system waits for the LED 30a and the signal detection circuit 76 to be stabilized. Then a reflected light intensity from the test piece 1 is detected by the photosensor 30b. At this time, when the measured reflected light intensity is within a predetermined range stored in the ROM 73, the process proceeds to step S10 where a normal measurement process is performed. However, when out of the predetermined range, the process proceeds to step S8 where the buzzer 79 is turned on, and "Err" is displayed on the display section 51. The process waits for the test piece 1 to be unloaded, and then the process returns to step S2.

As described above, the process proceeds from step S7 to step S8 when the test piece 1 is reversely inserted into the main body of the device, the LED 30a irradiates the blood in the opening 4, and the reflected light enters the photosensor 30b. As mentioned earlier, the color of the test paper of the opening 2a is substantially white at first, and its density increases with the lapse of time. Meanwhile, blood is applied to the opening 4, and its color is substantially fixed at a high density. Therefore, if the test piece 1 is inserted into the opening 24 of the device reversely as shown in FIG. 1, the measured density value is abnormally high since the color of the blood applied to the opening 4 is measured.

Figure 7:
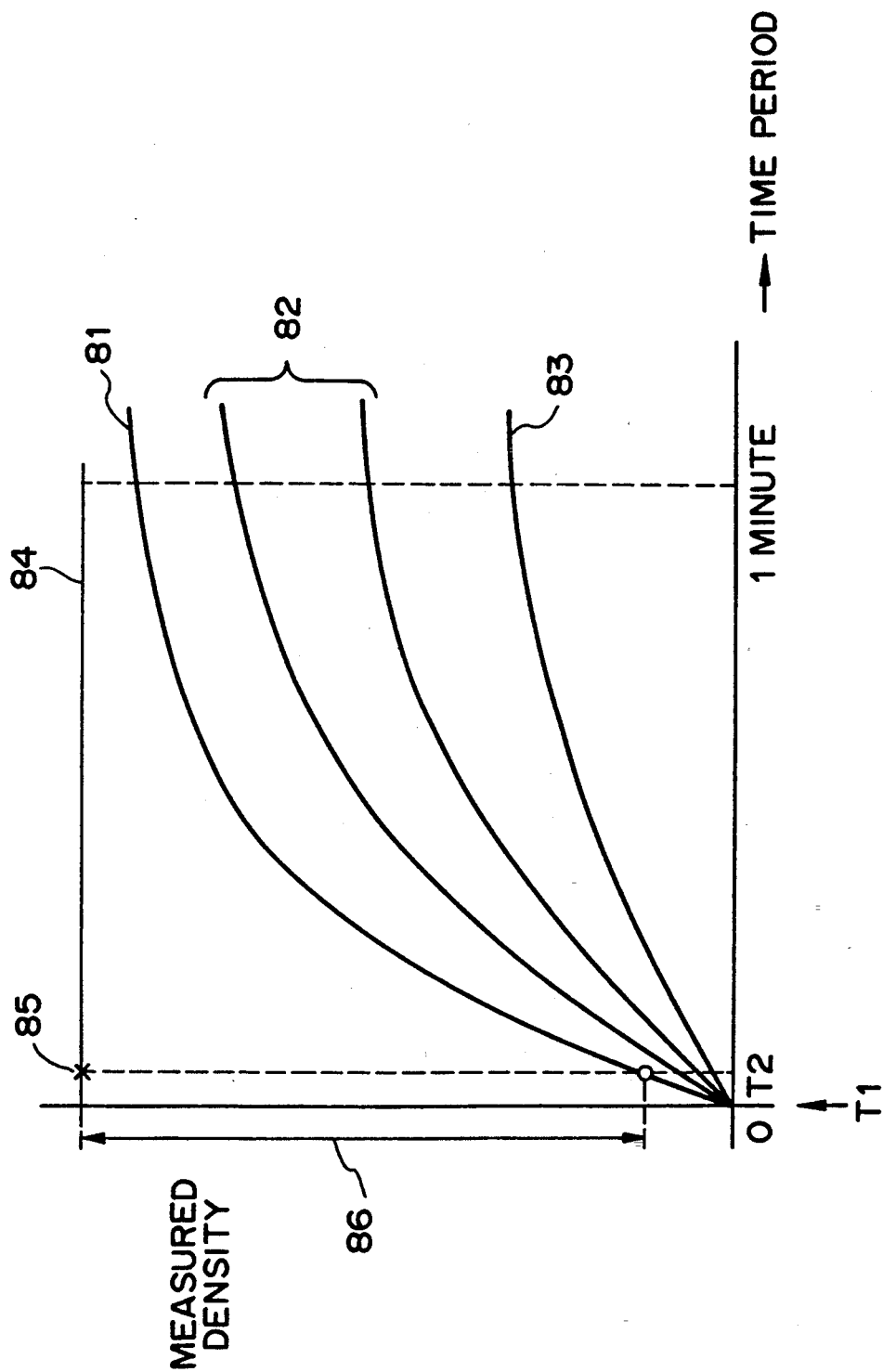
FIG. 7 is a view showing the relationship between the time period during which a test piece applied with blood is measured and the measured concentration.

FIG. 7 is a view showing the relationship between the time period during which a test piece applied with blood is measured and the measured density.

When the test piece 1 is loaded into the main body of the device at timing T1, the density of the color of the test piece 1 increases gradually as shown by the curbs of 81 through 83. In the blood sugar measuring device 50 of this embodiment, a measurement is made when it takes approximately one minute after the test piece 1 is inserted. Numerals 81, 82, and 83 indicate changes in the reaction color of the test paper of the test piece 1 in the case of a high blood sugar value, a medium blood sugar value, and a low blood sugar value, respectively. In contrast to these, numeral 84 indicates a measured density of the color (the color of the opening 4) of the blood. This measured density is kept at a fixed, high density state irrespective of the time period. Therefore, when reflected light intensity is measured using the photosensor 30b at timing T2, the discrepancy in measured densities is great, as shown by the line with double arrows 86, in cases where the test piece 1 is reversely inserted and correctly inserted. It can be detected, whether the test piece 1 has been reversely inserted.

Figure 8:
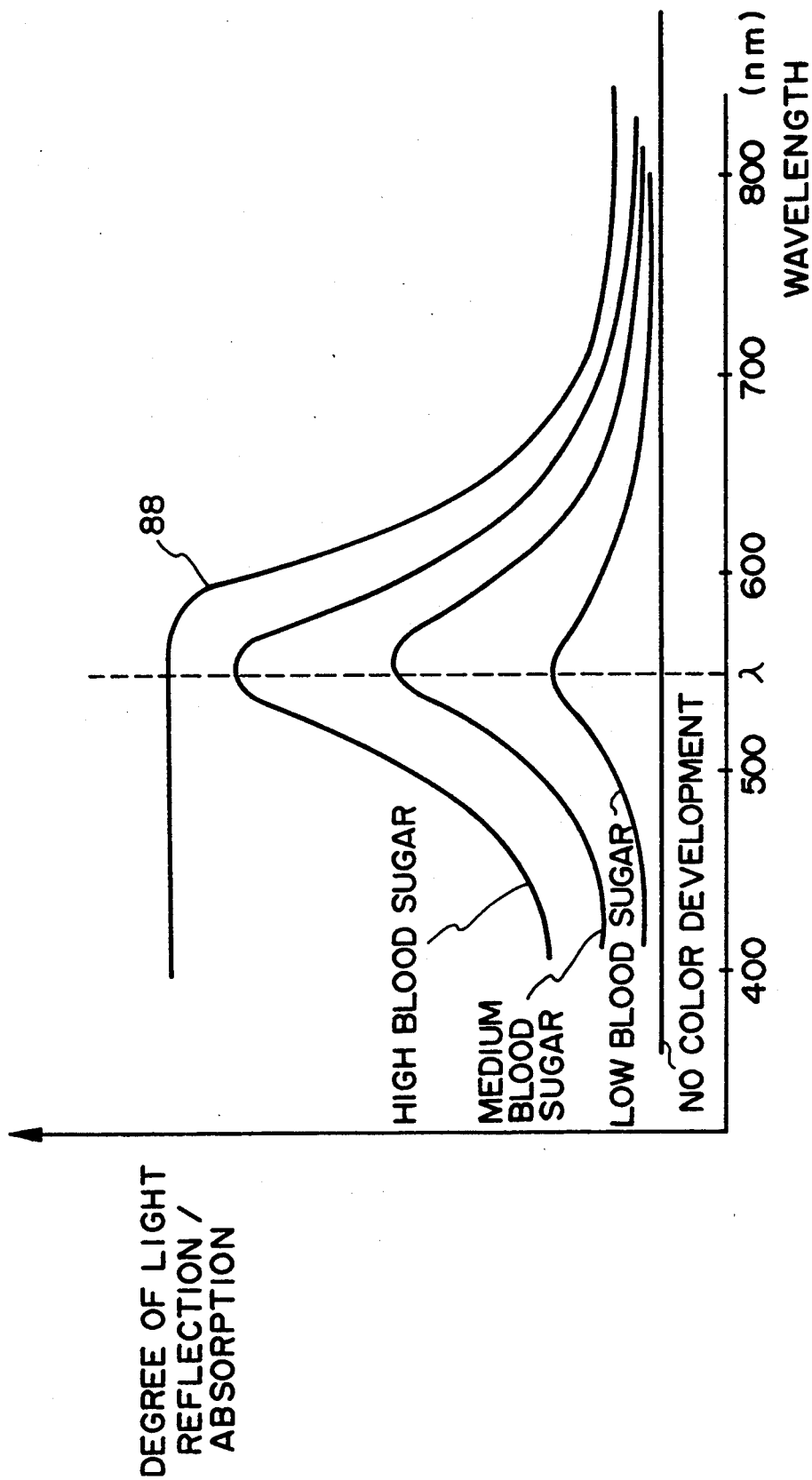
FIG. 8 is a view showing the relationships between the degrees of light reflection and absorption by test paper and blood with respect to the wavelength of light.

FIG. 8 is a view showing the relationship between the degrees of light reflection and absorption by test paper and blood with respect to the wavelength of light.

The curb 88 shows the degree of light absorption by blood (the opening 4 side). The other curbs show the degree of light absorption by test paper (the opening 2a side). Therefore, if the reflected light intensity from the test paper is detected using the LED 30a which emits light of a wavelength λ (e.g. 500 to 600 nm), it can be easily discriminated only by the reflected light intensity, whether the reflected light is from the test paper or from the blood, i.e., whether it is from the opening 4 or the opening 2a. As a result, it is discriminated whether the test piece 1 has been inserted normally (the direction shown in FIG. 1) or reversely.

When it is detected in step S7 that the test piece 1 has been normally inserted, the process proceeds to step S10 where "60" seconds is displayed on the display section 51 and a measurement process is started. At this time, the LED 30a is turned off in order to reduce power consumption. Next, the system waits for one minute in step S11. After the lapse of one second, the process proceeds to step S12 where the buzzer 79 is turned on, the time period is counted down by one second and the remaining time period is displayed. These time periods may be measured by the timer 78 or by a control program stored in the ROM 73. When one minute has elapsed in step S13, the process proceeds to step S16 where a measurement process is performed. During this period, if it is detected in step S14 that the test piece 1 has been unloaded, the process proceeds to step S15 where an error message is displayed on the display section 51 and the buzzer 79 is turned on.

In step S16, a signal is output to the LED driver 75 to cause the LED 30a, which has been off, to emit light. In step S17, the reflected light intensity detected by the photosensor 30b is read. This reflected light intensity is output from the signal detection circuit 76, converted to a digital signal by the control section 70, and input to the CPU 72. When the reflected light intensity is thus input, the process proceeds to step S18 where the LED 30a is turned off, and the blood sugar value is determined on the basis of the reflected light intensity. The above procedure may be performed in such a way that, for example, a table including the values of reflected light intensity corresponding to the blood sugar value is previously stored in the ROM 73 or the like, and the blood sugar value may be determined by referring to the table on the basis of the input reflected light intensity.

If the blood sugar value is determined in the above way, the process proceeds to step S19 where the measurement result is displayed on the display section 51. At this time, if, for example, the measured value is smaller than a predetermined range, "Lo" is displayed on the display section 51; if greater than the predetermined range, "Hi" is displayed, thus informing an operator that the measured value is abnormal.

When the measurement process is completed, it is checked in steps S20 and S22 whether or not the storage stop switch 54 has been depressed within a predetermined time period (about 3 min.). If the switch 54 is not depressed within the predetermined time period, the process proceeds to step S23 where the measurement result is stored in the RAM 74 along with the current date and time information. If the storage stop switch 54 is depressed within the predetermined time period, the process proceeds to step S21 where the display section 51 displays that storage is stopped, and then the process returns to step S9.

As has been explained above, according to this embodiment, blood is applied to the test piece 1, and the test piece 1 is immediately loaded into the device 50, whereby the blood sugar value of the blood under measurement is measured automatically. At this time, if the test piece has been reversely inserted, an error message is displayed immediately. Therefore, an operator may once unload and correctly insert the test piece 1 again for measuring the blood sugar value.

Figure 9:
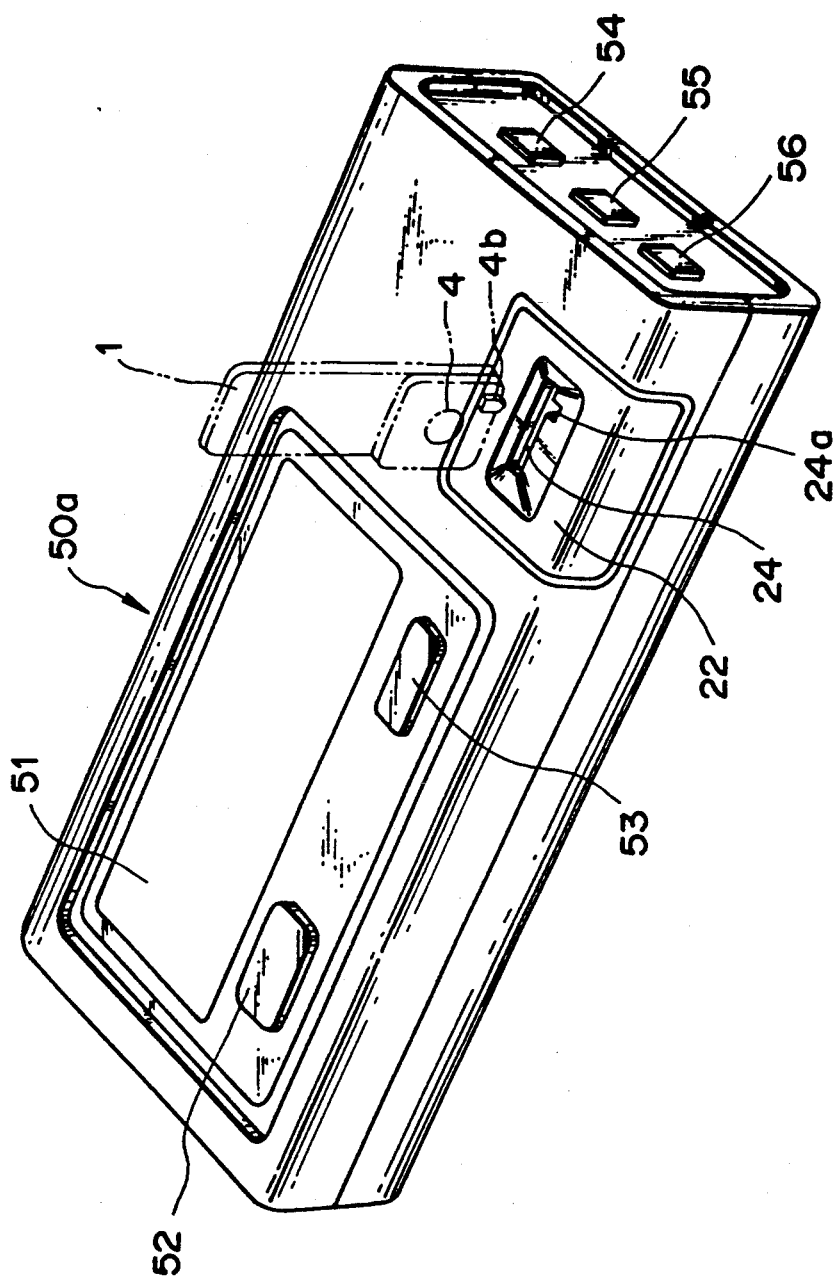
FIG. 9 is a perspective view of the exterior of an automatic blood sugar measuring device in a second embodiment of this invention.

FIG. 9 is a perspective view of an appearance of an automatic blood sugar measuring device 50a of a second embodiment of this invention. Parts common to those in FIG. 1 are given the same numerals, and an explanation thereof is omitted.

In this embodiment, a projection 4b is formed on the test piece 1. This projection 4b engages with the cutout section 24a in the opening 24 of the main body of the device 50a, thus preventing the test piece 1 from being reversely inserted.

Figure 10A:
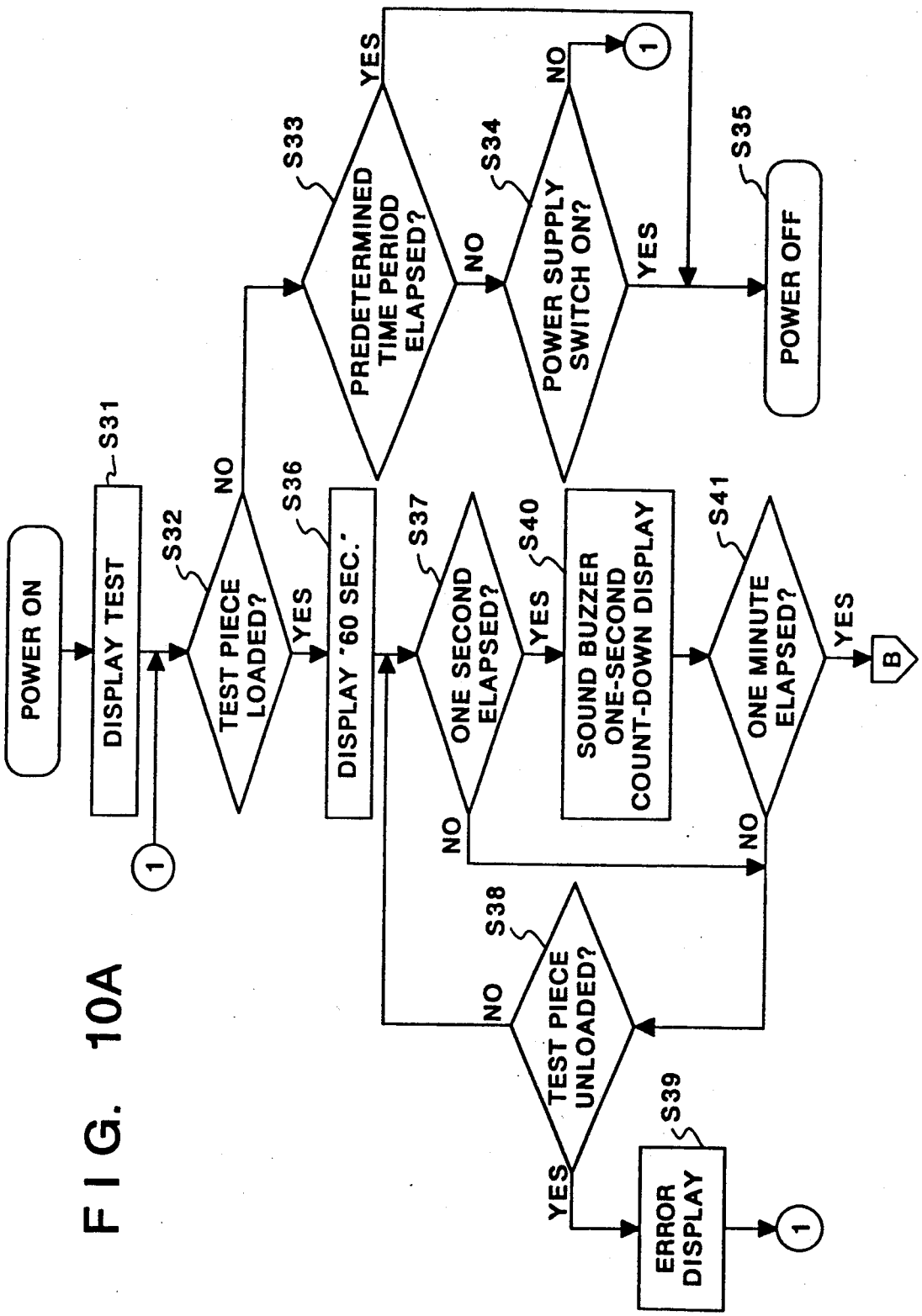
FIGS. 10A and 10B are flowcharts illustrating a measurement process of the blood sugar measuring device in the second embodiment.
Figure 10B:
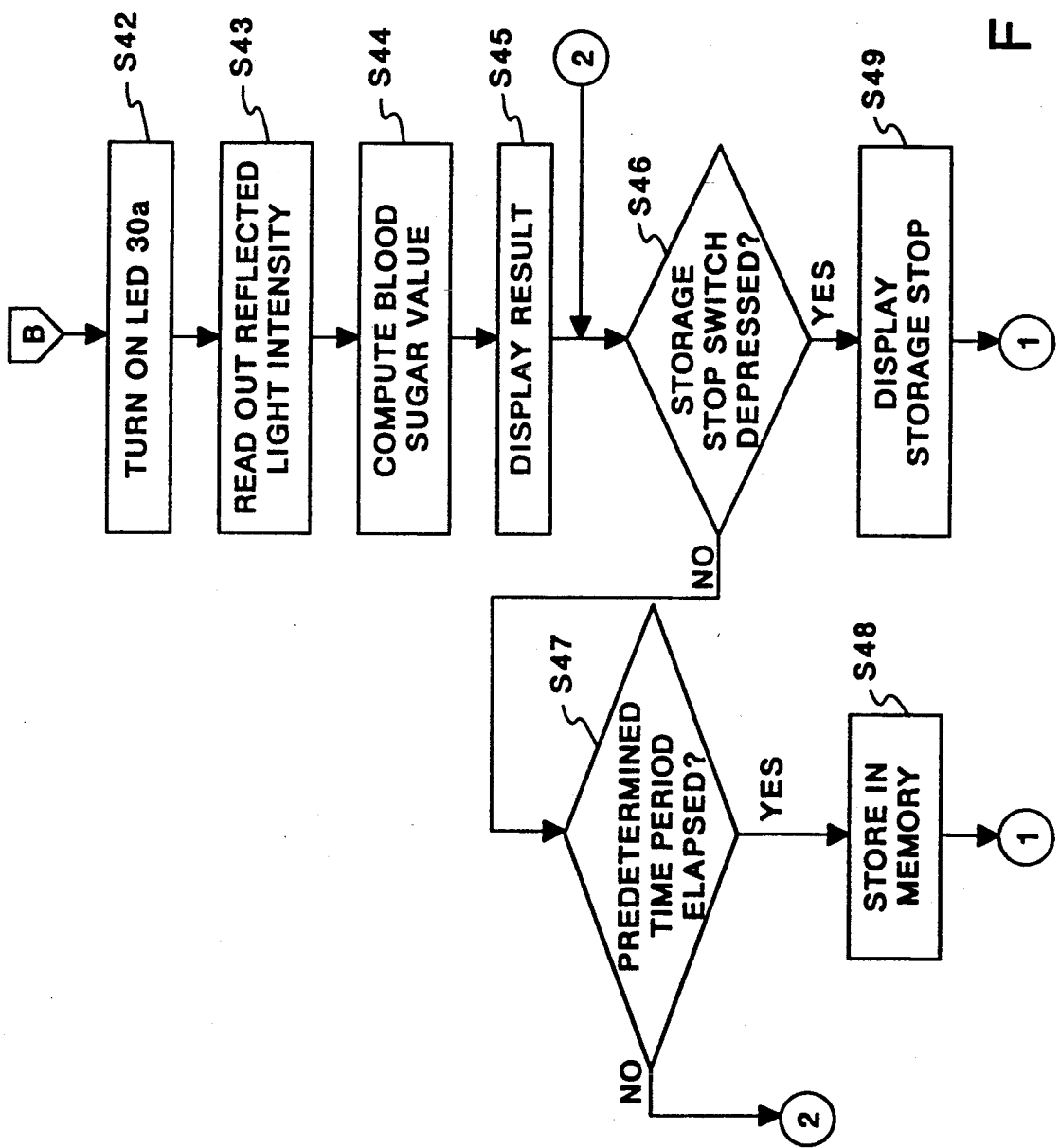

A measurement process in the automatic blood sugar measuring device 50a equipped with a reverse insertion prevention mechanism is shown in a flowchart in FIG. 10. As is apparent from a comparison with the flowchart of FIG. 6, this measurement process is the same as the flowchart of FIG. 6 except that process steps (steps S6 through S9) for checking the reverse insertion of the test piece 1 are not included. Therefore, an explanation of the flowchart of FIG. 10 is omitted because the explanation of steps S10 through S23 of FIG. 6 previously given may be used.

Figure 11:
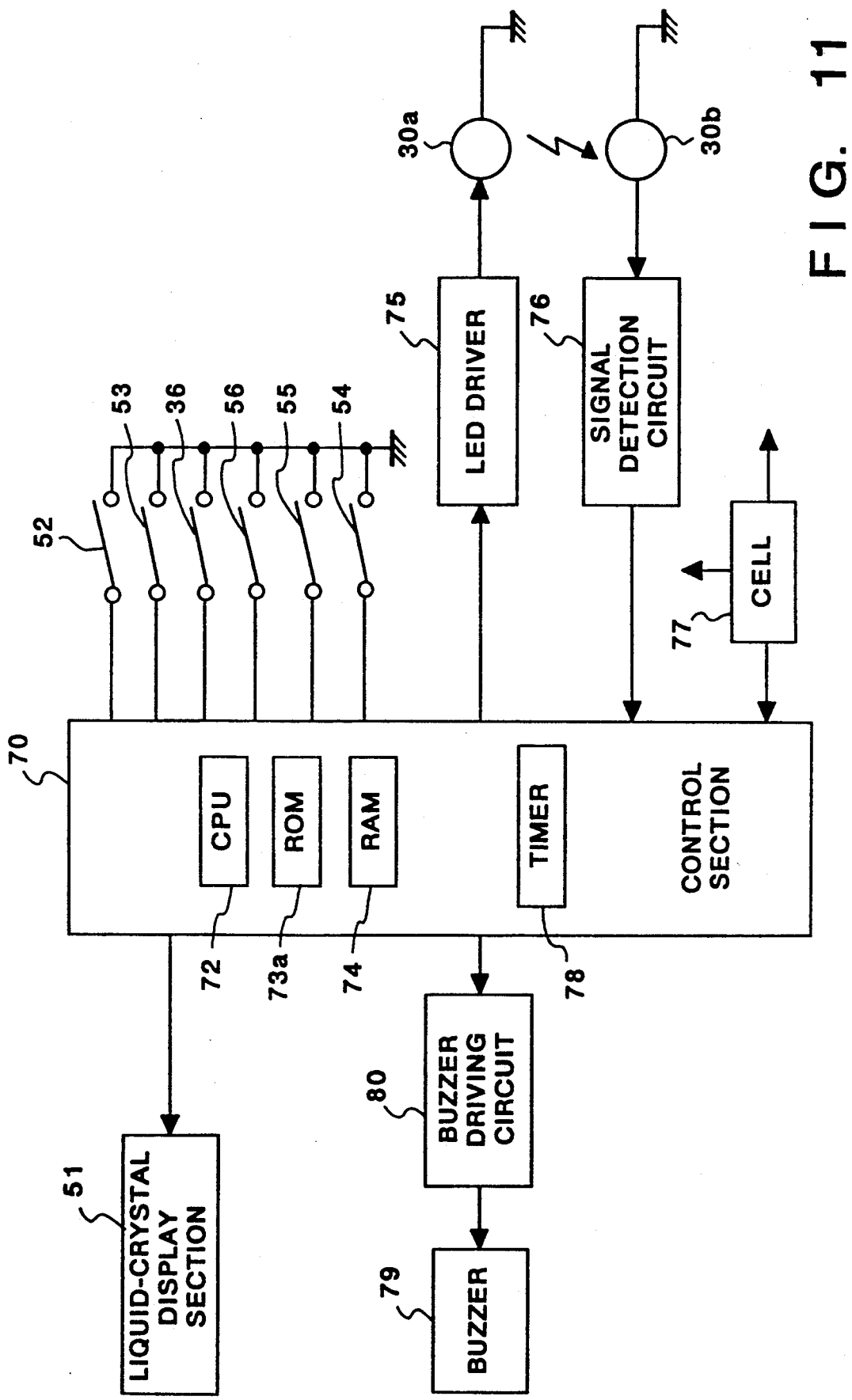
FIG. 11 is a block diagram illustrating the construction of the automatic blood sugar measuring device in a third embodiment of the present invention.

FIG. 11 is a block diagram schematically illustrating the construction of the automatic blood sugar measuring device of a third embodiment. Parts common to those used in FIG. 2 are given the same numerals, and an explanation thereof is omitted.

This embodiment differs from the embodiment shown in FIG. 2 in that the buzzer driving circuit 80 is provided in the circuit. This buzzer driving circuit 80 is adapted to change, by instructed from the control section 70, a volume, a tone, and a length of sound of the buzzer 79 by means of changing a voltage or a frequency for driving the buzzer 79.

Figure 12:
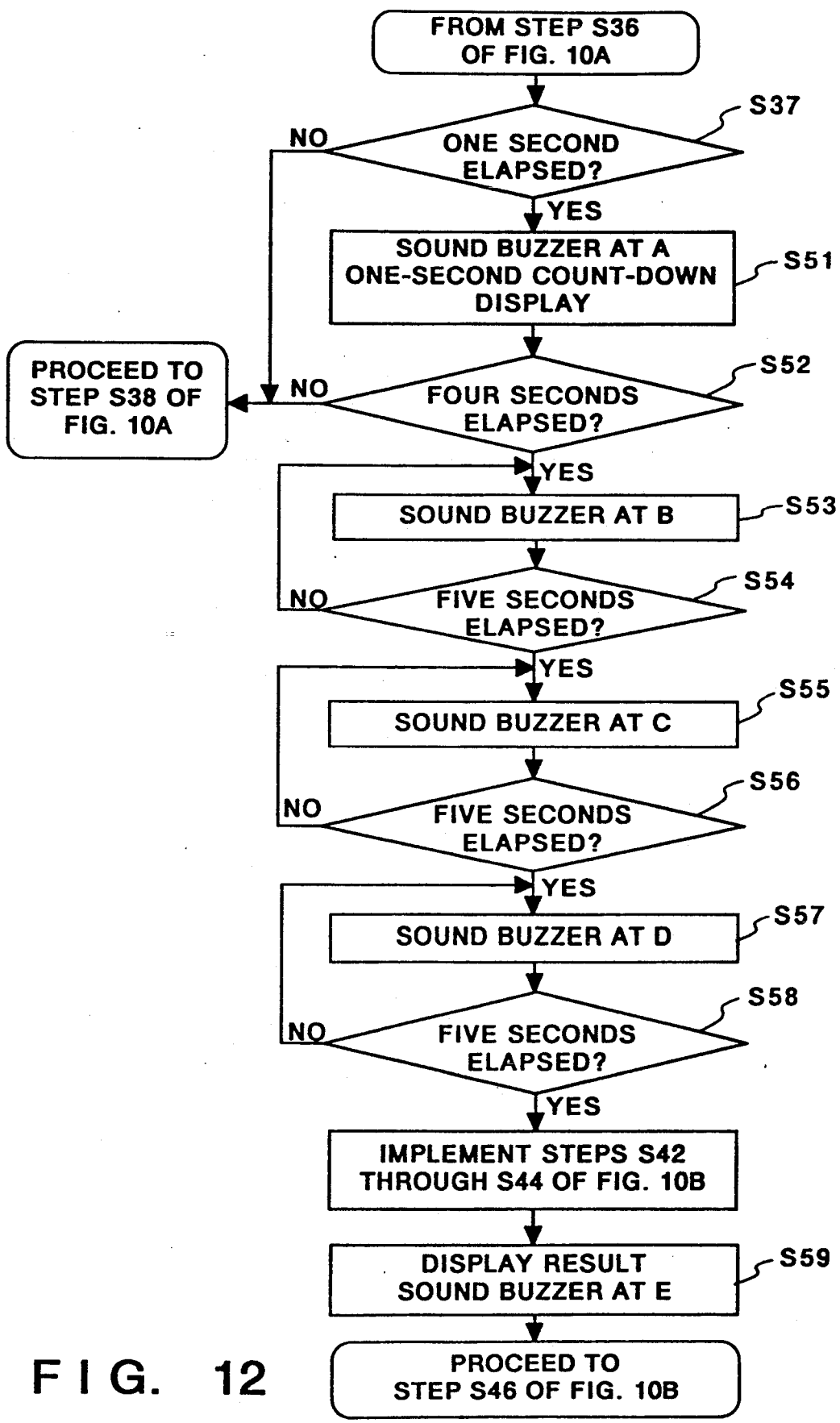
FIG. 12 is a flowchart illustrating a measurement process in the blood sugar measuring device in the third embodiment.

FIG. 12 is a flowchart illustrating the measurement process in the blood sugar measuring device of the third embodiment shown in FIG. 11. The control programs for performing this process are stored in the ROM 73a. In this flowchart, steps identical to the steps S of FIG. 10 are given the same step numbers, and this flowchart mainly shows steps different from the steps of the flowchart of FIG. 10.

In the flowchart of FIG. 12, in step S51, the buzzer 79 is sounded for example at a frequency A for 45 seconds. Thereafter, the frequency at which the buzzer 79 sounds is changed from frequency B (steps S53 and S54)→to frequency C (steps S55 and S56)→to frequency D (steps S57 and S58) every five seconds. When the measurement is terminated finally, the buzzer 79 is sounded at a frequency E in step S59.

These A to E are not limited to frequencies. For example, they may correspond to the length or type of sound that the buzzer 79.

As has been explained above, according to this embodiment, blood is applied to the test piece 1, and the test piece 1 is immediately loaded into the device 50, whereby the blood sugar value of the blood under measurement is measured automatically. Hence, blood sugar can be measured easily and accurately by anyone. During the reaction time period required for a measurement, the measured time period is counted down (or counted up) and displayed. This informs an operator of a measurement in process, as well as the status of the measurement procedure, thereby giving the operator a relief.

Figure 13:
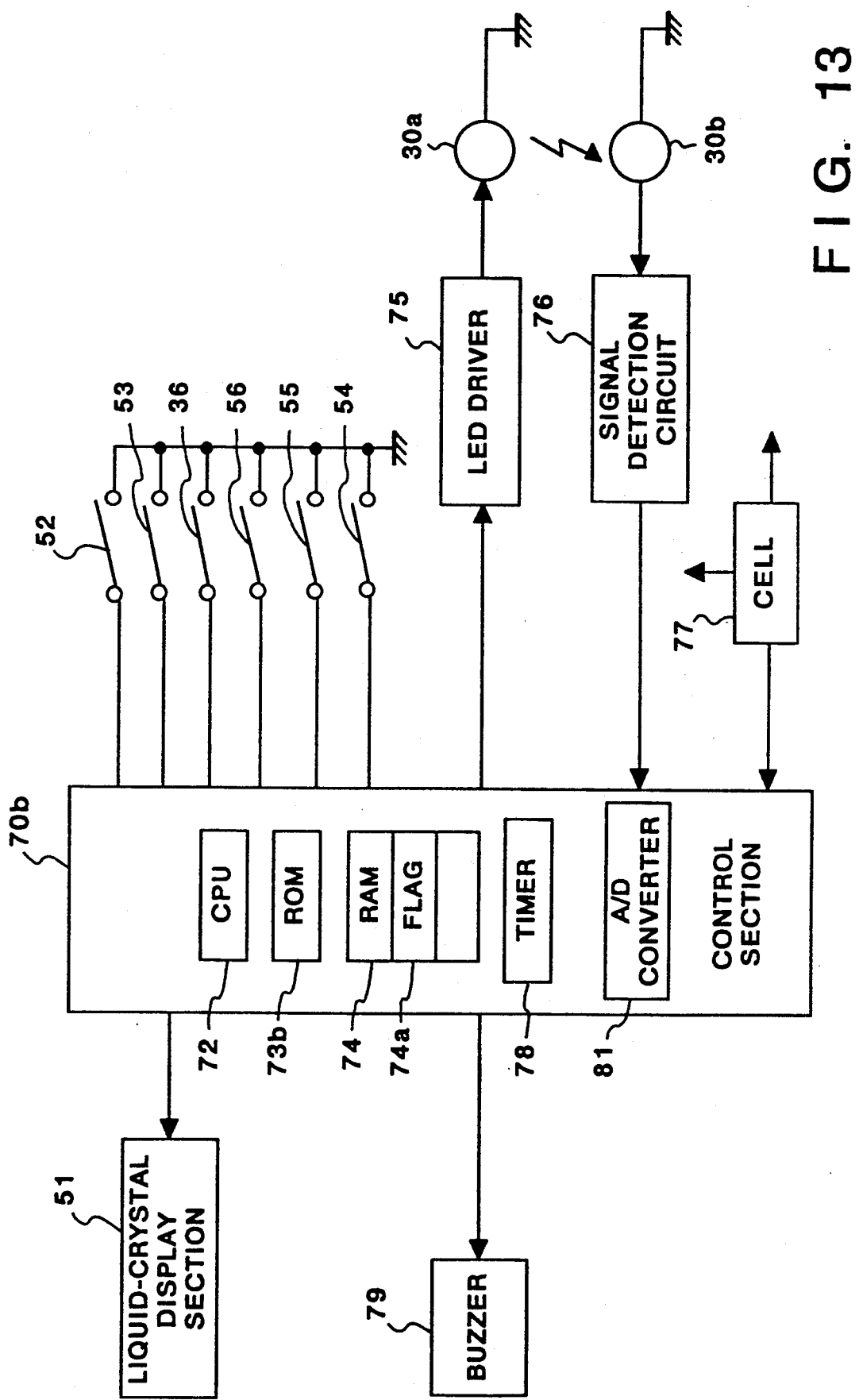
FIG. 13 is a block diagram illustrating the construction of the automatic blood sugar measuring device in a fourth embodiment of the present invention.

FIG. 13 is a block diagram illustrating the construction of the automatic blood sugar measuring device of a fourth embodiment of the present invention. Parts identical to those used in the above-mentioned first to third embodiments are given the same numerals, and an explanation thereof is omitted.

In FIG. 13, numeral 70b denotes a control section which controls the whole device. This control section comprises a CPU 72 such as a microprocessor, a ROM 73b for storing control programs for the CPU 72 shown in the flowcharts of FIGS. 14 to 15 and various kinds of data, and a RAM 74 used as a work area for the CPU 72 as well as a storage for measurement results and the measurement date and time. In this RAM 74, a flag 74a is provided for indicating whether or not date and time information has been input. This flag 74a is set when information on the date and time is input by depressing the setting switch 55.

Figure 14A:
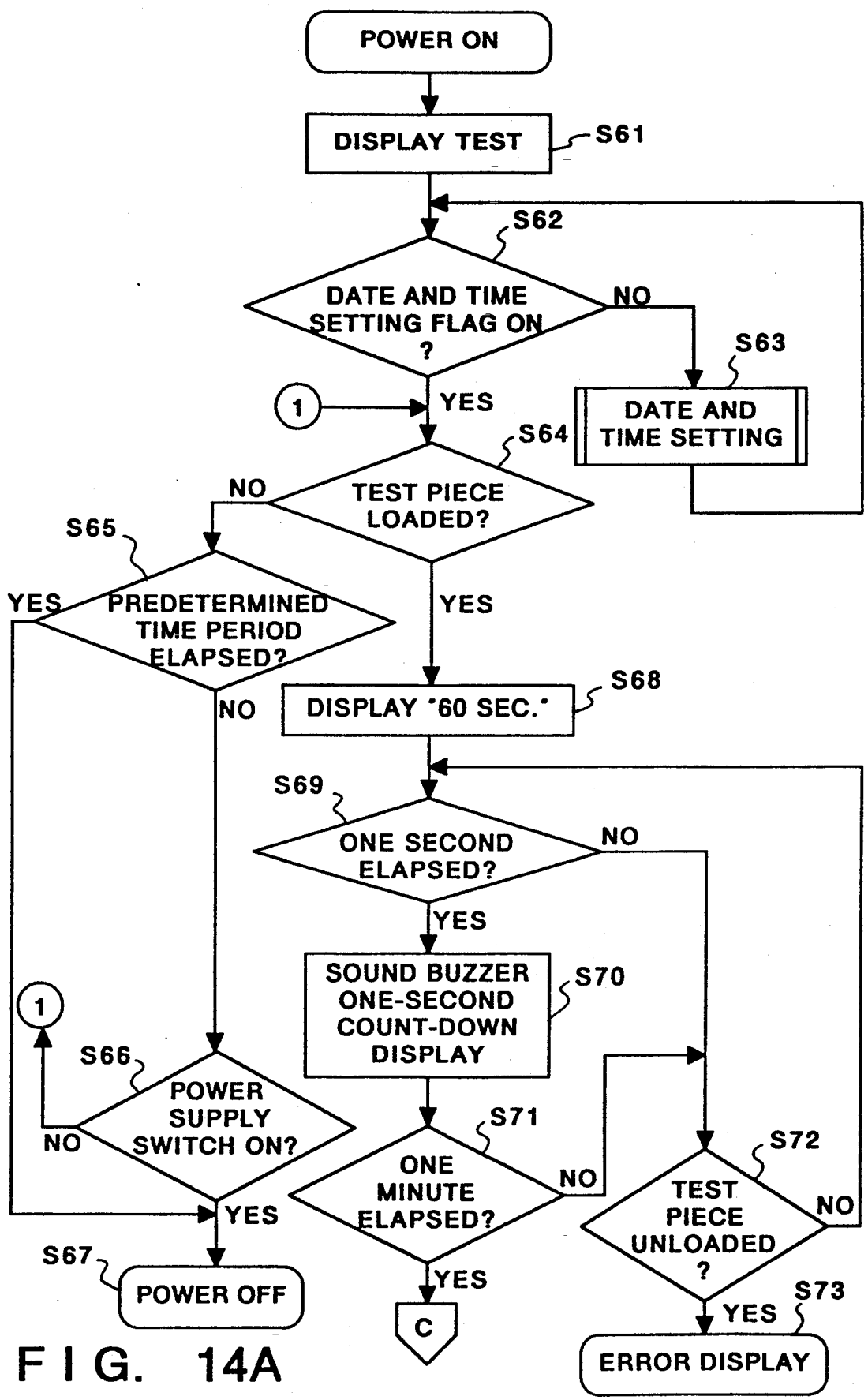
FIGS. 14A and 14B are flowcharts illustrating the measurement process in the blood sugar measuring device in the embodiment.
Figure 14B:
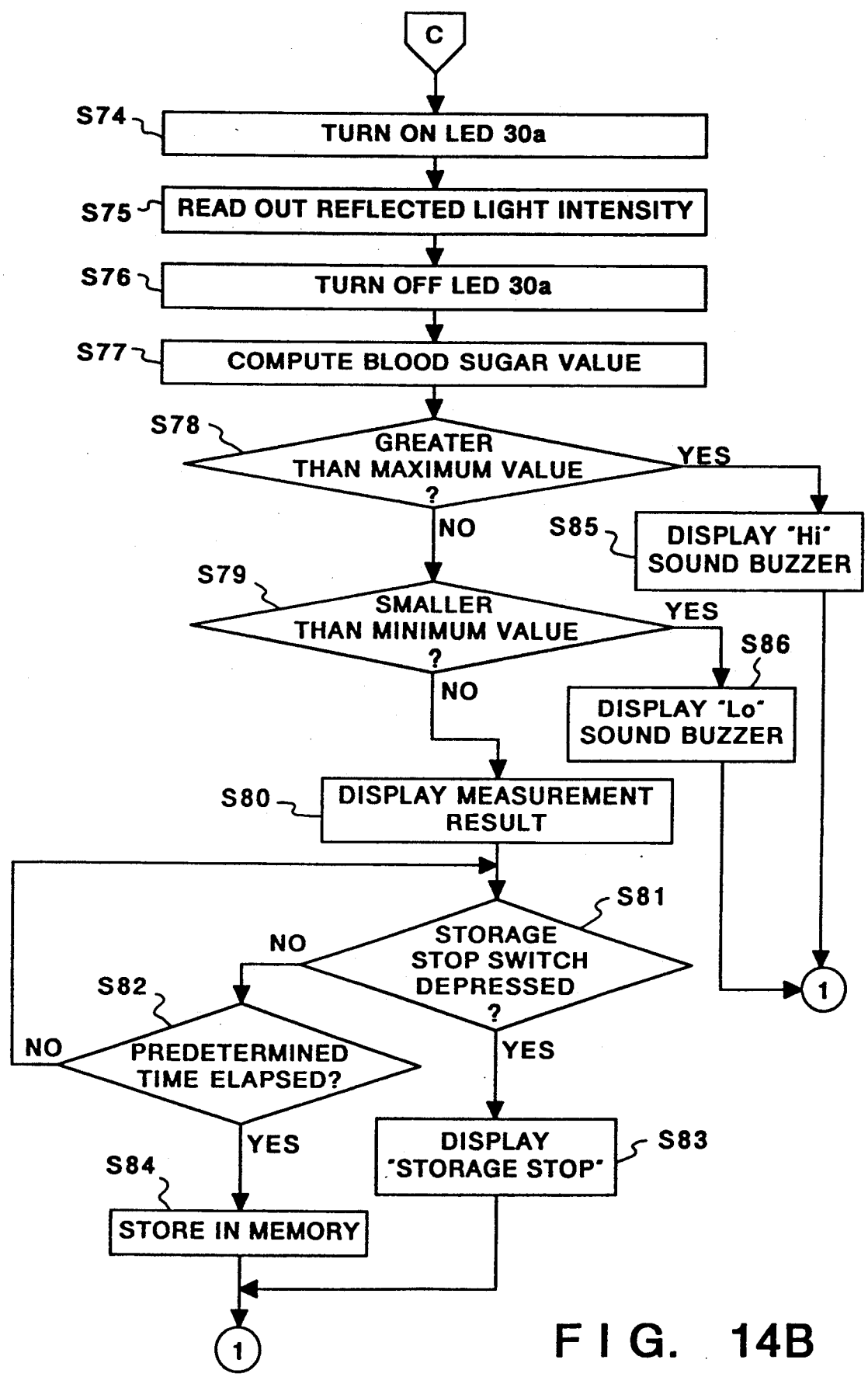
Figure 15:
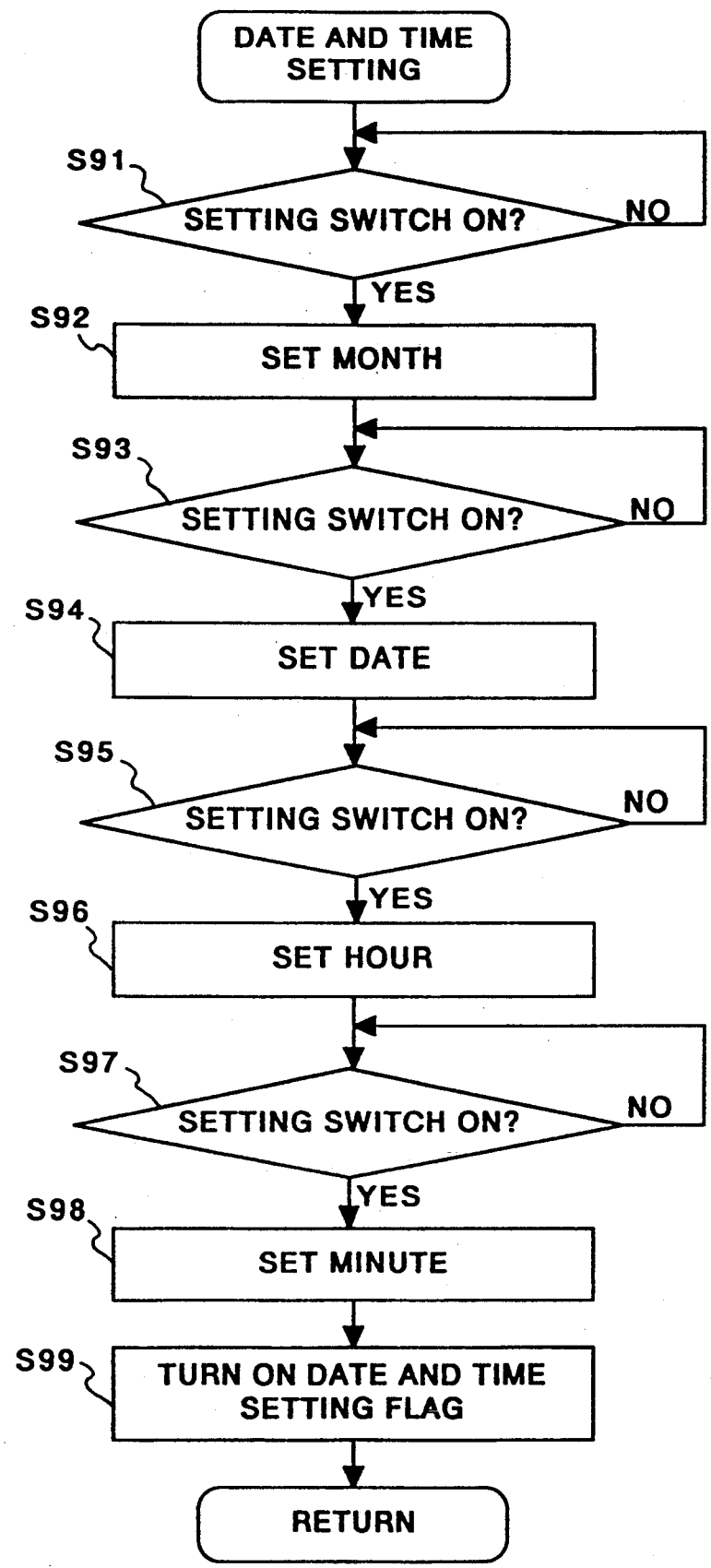
FIG. 15 is a flowchart illustrating a date and time setting process in step S63 of FIG. 14.

FIGS. 14 and 15 are flowcharts illustrating the operations in the blood sugar measuring device of the fourth embodiment. Control programs for performing these operations are stored in the ROM 73b.

The operations shown in FIG. 14 are started when the power supply switch 52 of the device is depressed to turn the power supply on. In step S61, in order to confirm whether or not the display section 51 is functioning normally, all items which can be displayed are displayed on the display section 51 for several seconds. Next, the process proceeds to step S62 where it is checked whether or not the date and time setting flag 74a in the RAM 74 is set. This flag 74a is set when date and time data is once input by the setting switch 55 and thereafter will not be reset until all information is erased by an all-clear switch, not shown.

If the date and time data has not been input, the process proceeds to step S63 where the operation for inputting date and time data shown by the flowchart of FIG. 15 is performed.

When the date and time data has been input (the flag 74a is on), the process proceeds to step S64 where it is checked whether or not the test piece 1 has been loaded by determining whether or not the switch 36 is on. If the switch 36 is not on (the test piece 1 has not been loaded), the process proceeds to step S65 where it is checked whether or not a predetermined time period (for example, five minutes) has elapsed. If the predetermined time period has elapsed, the process proceeds to step S67 where the power supply of the device 50 is turned off. If the predetermined time period has not yet elapsed in step S65, the process proceeds to step S66 where it is checked whether or not the power supply switch 52 has been depressed. When yes, the process proceeds to step S67 where the power supply of the device 50 is turned off. In the power-off state of step S67, the power supply to the display section 51 is only interrupted. Since power is kept supplied to both the RAM 74 and the control section 70, the contents of the RAM 74 will be maintained.

When it has been detected in step S64 that the test piece 1 has been loaded, the process proceeds to step S68 where "60" seconds is displayed on the display section 51, and the system waits for one second in step S69. After the lapse of one second, the process proceeds to step S70 where the buzzer 79 is turned on, the time period is counted down by one second and the remaining time period is displayed. These time periods may be measured by the timer 78 or by a control program stored in the ROM 73. When one minute has elapsed in step S71, the process proceeds to step S73 where a measurement process is performed. During this period, if it is detected in step S72 that the test piece 1 has been unloaded, the process proceeds to step S73 where an error message is displayed on the display section 51 and the buzzer 79 is turned on.

In step S74, a signal is output to the LED driver 75 to cause the LED 39a, which has been off, to emit light. In step S75, the reflected light intensity detected by the photosensor 30b is read. This reflected light intensity is output from the signal detection circuit 76, converted to a digital signal by the control section 70, and input to the CPU 72. When the reflected light intensity is thus input, the process proceeds to step S76 where the LED 30a is turned off. Next, in step S77, the blood sugar value is determined on the basis of the reflected light intensity. The above procedure may be performed in such a way that, for example, a table including the values of reflected light intensity corresponding to the blood sugar values is previously stored in the ROM 73b or the like, and the blood sugar value may be determined by referring to the table on the basis of the input reflected light intensity.

When the blood sugar value has been determined as described above, the process proceeds to step S78 where it is checked whether or not the measurement result is greater than an allowable maximum value. If the result is smaller than the allowable maximum value, the process proceeds to step S79 where the result is compared with an allowable minimum value. If the measurement result is between the allowable maximum value and the allowable minimum value, the process proceeds to step S81 where the measurement result is displayed on the display section 51. At this time, if the measured value is smaller than the allowable minimum value, "Lo" is displayed on the display section 51 in step S86; if greater than the allowable maximum value, "Hi" is displayed in step S95, thus notifying an operator that the measured value is abnormal.

Next, in steps S81 and S82, it is determined whether or not the storage stop switch 54 described above has been depressed within a predetermined time period (about 3 min). If the switch 54 is not depressed within the predetermined time period, the process proceeds to step S84 where the measurement result is stored in the RAM 74 along with the current date and time information. If the storage stop switch 54 is depressed within the predetermined time period in step S81, the process proceeds to step S83 where the display section 51 indicates that storage is stopped, and then the process returns to step S64.

FIG. 15 is a flowchart illustrating the date and time setting process of step S63 of FIG. 14.

In step S91, the system waits for the setting switch 55 to be depressed. If it is depressed, the process proceeds to step S92 for updating month data, in which month data is blinked on and off, and month data is increased by 1 each time the change switch 56 is depressed. When desired month data to be input is displayed, the setting switch 55 is depressed. To thereby store the month data which is currently displayed on the display section 51 as month information in the RAM 74.

Hereinafter, in the same way as the above, when the setting switch 55 is turned on in step S93, day data is blinked on and off. In step S94, day data set by the change switch 56 is stored by the setting switch 55. Similarly, hour data is set and stored in steps S95 and S96, and minute data is set and stored in steps S97 and S98. When month, day, and hour data are stored in this manner, the date and time setting flag 74a is set in step S99.

Though not particularly shown in this embodiment, the name, sex, age, body temperature, blood pressure, etc. of a person under inspection can be entered and set by utilizing alphanumeric keys or numeric keys.

The date and time data thus set is constantly updated according to the information from the timer 78. When the blood sugar value is measured, the result of the measurement is stored in the memory (the RAM 74) together with the date and time data. Whenever the storage retrieval switch is depressed, the measurement result can be read out and displayed on the display section 51 along with the stored date and time data.

As has been explained above, according to this embodiment, when the date and time information, indispensable in storing and referring to the measurement results of the blood sugar values, has not been stored, the blood sugar value measurement process is automatically prohibited, thus effectively utilizing the measured blood sugar value information without rendering it useless. In this embodiment, the supplement information has been explained as the data of date and time, but this invention is not limited to this embodiment. For example, the supplement information would be a name of person under inspection (if enable to input the name) and the other identifiable information.

In this embodiment, a blood sugar measurement has been explained by way of example. However, the present invention is not limited to this device. It can be applied to, for instance, an analysis device for uric acids, GTO, GPT, cholesterol, or the like. Regarding a specimen, for example, body fluids such as urine and saliva may be considered in addition to blood.

As many widely different embodiments of the present invention can be made without departing from the spirit and scope thereof, it is to be understood that the invention is not limited to the specific embodiments thereof except as defined in the appended claims.

What is claimed is:

1. A system which measures the constituent concentration of a specimen, comprising:

a test piece having a test material which develops coloring as a result of a reaction with the constituents of said specimen, said test piece also including a first opening on one side thereof and a second opening on the other side thereof at a location corresponding to said first opening, said first opening provided for applying a specimen to said test material;

a measuring apparatus for receiving the test piece, said measuring apparatus including:

test piece detection means for detecting that said test piece has been loaded into a main body of the apparatus;

irradiation means for irradiating said test piece with light when the loading of said test piece is detected by said test piece detection means;

judgment means for detecting whether or not an intensity of light reflected from said test piece is within a predetermined range and for judging whether or not the reflected light is reflected through said second opening;

notifying means for notifying that a measurement using said test piece is impossible when said judgment means judges that the reflected light is not reflected through said second opening;

detection means for detecting the intensity of light emitted by said irradiation means and reflected through said second opening; and measurement means for determining the constituent concentration of said specimen on the basis of the intensity of the reflected light detected by said detection means.

2. The system according to claim 1, wherein said test material includes a liquid development layer in which said specimen is infiltrated through said first opening side, a reagent layer which reacts with said specimen, a liquid absorption layer for absorbing said specimen which is not absorbed in said liquid development layer on said first opening side, and a transparent layer between said reagent layer and said second opening.

3. A system which measures the constituent concentration of a specimen, comprising:

a test piece having a test material and a first opening on one side thereof and a second opening on the other side thereof at a location corresponding to said first opening, said first opening provided for applying a specimen to said test material therethrough, and said second opening for irradiating said test material with light, wherein said test material includes a liquid development layer in which said specimen is infiltrated through said first opening, a reagent layer which reacts with said specimen and a transparent layer between the reagent layer and the second opening;

a measuring apparatus for receiving the test piece, said measuring apparatus including:

test piece detection means for detecting that said test piece has been loaded into a main body of the apparatus;

judgment means for irradiating said test piece with light when the loading of said test piece is detected by said test piece detection means and for judging whether or not reflected light is reflected through said second opening based on the intensity of the reflected light from said test piece;

notifying means for notifying that a measurement using said test piece is impossible when said judgment means judges that the reflected light is not reflected through said second opening;

irradiation means for irradiating said reagent layer through said second opening with light if said judgment means judges that the reflected light is reflected through said second opening;

detection means for detecting the intensity of a light emitted by said irradiation means and reflected through said second opening from said reagent layer;

measurement means for determining the constituent concentration of the specimen applied to said reagent layer on the basis of the intensity of the reflected light detected by said detection means; and measuring control means for controlling so as to allow said measurement means to start measuring at approximately the moment that a predetermined time period has elapsed after the loading of said test piece is detected by said test piece detection means, said predetermined time period approximating the time required for the specimen to infiltrate through the liquid developing layer to the reagent layer and to react with the reagent layer.

4. A system which measures the constituent concentration of a specimen, comprising:

a test piece having a test material having a first opening on one side thereof, a second opening on the other side thereof at a location corresponding to said first opening and the test material between said first and second openings, said first opening provided for applying a specimen to the test material therethrough, and said second opening provided for irradiating said test material with light, wherein said test material includes a liquid development layer in which said specimen is infiltrated through said first opening, a reagent layer which reacts with said specimen, and a transport layer between said reagent layer and the second opening;

a measuring apparatus for receiving the test piece, said measuring apparatus including:

a main body;

test piece detection means for detecting that said test piece has been loaded into a main body of the apparatus;

judgment means for irradiating said test piece with light when the loading of said test piece is detected by said test piece detection means and for judging whether or not a reflected light is reflected through said second opening based on an intensity of the light reflected from said test piece;

notifying means for notifying that a measurement using said test piece is impossible when said judgment means judges that the reflected light is not reflected through said second opening;

time measurement means for measuring a predetermined time period, if said judgment means judges that the reflected light is reflected through said second opening, in which said specimen infiltrates through the liquid development layer and a coloring of the reagent layer that reacts with the specimen is substantially complete, after said test piece detection means detects that said test piece has been loaded into the main body;

display means for displaying a time period at a predetermined time interval during the time measurement by said time measurement means;

irradiation means for irradiating said reagent layer through said second opening with light approximately the moment that the time measurement by said time measurement means is terminated, detection means for detecting the intensity of a reflected light through said second opening from said reagent layer of the light emitted by said irradiation means; and measurement means for determining the concentration of the constituents of said specimen applied to said reagent layer on the basis of the intensity of the reflected light detected by said detection means.

5. The system according to claim 4, wherein said display means displays the time period in seconds, and said measuring apparatus further comprising an informing means for generating a sound every second.

6. The system according to claim 5, wherein at least one out of the volume, tone and length of the sound generated by said notifying means is changed when a remaining time period with respect to said predetermined time period falls below a predetermined value during the time measurement by said time measurement means.

7. A system which measures the constituent concentration of a specimen comprising:

a test piece having a test material having a first opening on one side thereof and a second opening on another side thereof at a location corresponding to said first opening, said first opening provided for applying a specimen to said test material therethrough, and said second opening for irradiating said test material with light, wherein said test material includes a liquid development layer in which said specimen is infiltrated through said first opening, a reagent layer which reacts with said specimen, and a transport layer between the reagent layer and the second opening;

a measuring apparatus for receiving the test piece, said measuring apparatus including:

test piece detection means for detecting that said test piece has been loaded into of the apparatus;

judgment means for irradiating said test piece with light when the loading of said test piece is detected by said test piece detection means and for judging whether or not the reflected light is reflected through said second opening based on an intensity of the light reflected from said test piece;

notifying means for notifying that a measurement using said test piece is impossible when said judgment means judges that the reflected light is not reflected through said second opening;

irradiation means for irradiating said reagent layer with light, if said judgment judges that the reflected light is reflected through said second opening;

detection means for detecting the intensity of a reflected light from said reagent layer of the light emitted by said irradiation means;

measurement means for measuring the degree of the coloring developed by said reagent layer based on said intensity and determining the constituent concentration of said applied specimen based on the degree of the coloring;

storage means for storing measured results by said measurement means together with supplementary information including one of measurement date, measurement time, and identification data of a person under examination;

setting means for inputting and setting said supplementary information; and control means for controlling the measurement means so as to prohibit said measurement means for measuring when the supplementary information has not been input and set by said setting means.

8. The system according to claim 7, further comprising a timer means and an update means for updating date and time information of said supplementary information on the basis of the information from said timer means.

9. A system which measures the constituent concentration of a specimen, comprising:

a test piece having a test material and a first opening on one side thereof and a second opening on the other side thereof at a location corresponding to said first opening, said first opening provided for applying a specimen to said test material therethrough, and said second opening for irradiating said reagent layer with light and detecting the intensity of the reflected light therethrough, wherein said test material includes a liquid development layer in which said specimen is infiltrated through said first opening, a reagent layer which reacts with said specimen and a transparent layer between said reagent layer and the second opening;

a measuring apparatus for receiving the test piece, said measuring apparatus including:

a main body;

test piece detection means for detecting that said test piece has been loaded into a main body of the apparatus;

judgment means for irradiating said test piece with light when the loading of said test piece is detected by said test piece detection means and for judging whether or not the reflected light is reflected through said second opening based on the intensity of the reflected light from said test piece;

notifying means for notifying that a measurement using said test piece is impossible, when said judgment means judges that the reflected light is not reflected by said second opening;

storage means for storing measured constituent concentration valued together with supplementary information including measurement data and time data and identification data of a person under inspection;

setting means for inputting and setting said supplementary information;

determination means for determining whether or not said supplementary information including one of measurement data, measurement time, and identification data of the person under examination has been set;

time measurement means for measuring a predetermined time period in which said specimen infiltrated through a liquid developing layer and a coloring of the reagent layer reacting with the specimen is substantially completed after the loading of said test piece is detected by said test piece detection means, when said determination means determines that said supplementary information including measurement data, measurement time, and identification data of the person under examination has been set and when said judgment means judges that the reflected light is reflected through said second opening;

display means for displaying a time period at a predetermined time interval during the time measurement by said time measurement means;

irradiation means for irradiating said reagent layer through the second opening at approximately the moment that the time measurement by said time measurement means is terminated;

detection means for detecting the intensity of a reflected light through said second opening from said reagent layer irradiated by said irradiation means; and measurement means for determining the concentration of the constituents of said specimen applied to said reagent layer on the basis of the intensity of the reflected light detected by said detection means.

* * * * *

UNITED STATES PATENT AND TRADEMARK OFFICE
CERTIFICATE OF CORRECTION

PATENT NO. : 5,316,727
DATED : May 31, 1994
INVENTOR(S) : Yoshiro SUZUKI et al

It is certified that error appears in the above-identified patent and that said Letters Patent is hereby corrected as shown below:

In Column 11, line 23, delete "39a" and insert -- 30a --.

In Column 15, line 35, delete "light reflected" and insert -- reflected light --.

In Column 16, line 24, delete "through" and insert -- by --.

In Column 16, line 53, delete "through" and insert -- by --.

Signed and Sealed this

Thirteenth Day of September, 1994

Attest:

BRUCE LEHMAN

*Attesting Officer*　　　　*Commissioner of Patents and Trademarks*